US008889163B2

(12) United States Patent
DeGrado et al.

(10) Patent No.: US 8,889,163 B2
(45) Date of Patent: Nov. 18, 2014

(54) FACIALLY AMPHIPHILIC POLYMERS AS ANTI-INFECTIVE AGENTS

(75) Inventors: William F. DeGrado, Moylan, PA (US); Gregory N. Tew, Amherst, MA (US); Michael L. Klein, Ocean City, NY (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 2173 days.

(21) Appl. No.: 10/471,029

(22) PCT Filed: Mar. 7, 2002

(86) PCT No.: PCT/US02/06899
§ 371 (c)(1),
(2), (4) Date: Jun. 7, 2004

(87) PCT Pub. No.: WO02/072007
PCT Pub. Date: Sep. 19, 2002

(65) Prior Publication Data
US 2004/0202639 A1    Oct. 14, 2004

Related U.S. Application Data

(60) Provisional application No. 60/247,145, filed on Mar. 8, 2001.

(51) Int. Cl.
| | | |
|---|---|---|
| *A01N 25/34* | (2006.01) | |
| *A01N 43/56* | (2006.01) | |
| *A61K 31/136* | (2006.01) | |
| *A61K 31/16* | (2006.01) | |
| *A61K 31/132* | (2006.01) | |
| *C08G 73/10* | (2006.01) | |
| *C07C 211/27* | (2006.01) | |
| *C07C 279/06* | (2006.01) | |
| *A61K 31/74* | (2006.01) | |
| *C08G 18/28* | (2006.01) | |
| *A61L 15/44* | (2006.01) | |
| *C08G 73/22* | (2006.01) | |
| *C08G 61/10* | (2006.01) | |
| *A61L 31/16* | (2006.01) | |
| *C08G 61/02* | (2006.01) | |
| *C08G 61/12* | (2006.01) | |
| *C08G 18/32* | (2006.01) | |
| *A01N 25/10* | (2006.01) | |
| *A61L 27/54* | (2006.01) | |
| *A61L 29/16* | (2006.01) | |

(52) U.S. Cl.
CPC ............. *A61L 15/44* (2013.01); *A61K 31/74* (2013.01); *C08G 18/2865* (2013.01); *C08G 73/22* (2013.01); *C08G 2261/312* (2013.01); *A61L 2300/216* (2013.01); *C08G 61/10* (2013.01); *A61L 31/16* (2013.01); *C08G 61/02* (2013.01); *C08G 61/122* (2013.01); *A61L 2300/404* (2013.01); *C08G 18/3225* (2013.01); *A01N 25/10* (2013.01); *A61L 27/54* (2013.01); *A61L 29/16* (2013.01)

USPC ............ 424/404; 424/400; 424/403; 514/247; 514/616; 514/634; 514/655; 564/374; 564/157; 564/236; 564/389

(58) Field of Classification Search
None
See application file for complete search history.

(56) References Cited

U.S. PATENT DOCUMENTS

| | | |
|---|---|---|
| 3,409,662 A | 11/1968 | Larsen |
| 3,444,156 A | 5/1969 | de Montmollin et al. |
| 3,484,407 A | 12/1969 | Preston |
| 3,829,563 A | 8/1974 | Barry et al. |
| 4,038,416 A | 7/1977 | Mori et al. |
| 4,118,232 A | 10/1978 | Piller et al. |
| 4,252,951 A | 2/1981 | Jackson et al. |
| 4,343,788 A | 8/1982 | Mustacich et al. |
| 4,392,848 A | 7/1983 | Lucas et al. |
| 4,508,639 A | 4/1985 | Camps et al. |
| 4,515,910 A | 5/1985 | Rawls et al. |
| 4,762,899 A | 8/1988 | Shikinami |
| 4,826,829 A | 5/1989 | Eurkart et al. |
| 4,847,353 A | 7/1989 | Watanabe |
| 4,943,624 A | 7/1990 | Regen |
| 5,021,311 A | 6/1991 | Kato et al. |
| 5,071,648 A | 12/1991 | Rosenblatt |
| 5,073,564 A | 12/1991 | Roush et al. |
| 5,077,281 A | 12/1991 | Reinmüller |
| 5,219,965 A | 6/1993 | Valint, Jr. et al. |

(Continued)

FOREIGN PATENT DOCUMENTS

| | | |
|---|---|---|
| CH | 520 657 A | 3/1972 |
| CH | 525 898 A | 7/1972 |

(Continued)

OTHER PUBLICATIONS

Kim et al., 32 Macromolecules 1500 (American Chemical Society 1998).*
Ge et al., 39 Angew. Chem. Int. Ed. 3607 (Wiley-VCH 2000).*
Höger, S., et al., "Synthesis and Properties of Shape-Persistent Macrocyclic Amphiphiles with Switchable Amphiphilic Portions",1999, Chemistry-A European Journal, 4(12), pp. 2423-2434.*
Ge, P., et al., "Structural Characterization of a Cyclohexameric meta-Phenyleneethynylene Made by Alkyne Metathesis with In Situ Catalysts", 2000, Angewandte Chemie International Edition, 39(20), pp. 3607-3610.*
Kim, J., et al., "Nanoscale Fibrils and Grids: Aggregated Structures from Rigid-Rod Conjugated Polymers", 1999, Macromolecules, 32(5), pp. 1500-1507.*
Salamone J.C., "POlymeric Materials Encyclopedia", vol. 8, CRC Press, 1996.*

(Continued)

*Primary Examiner* — Michael G Hartley
*Assistant Examiner* — Lance Rider
(74) *Attorney, Agent, or Firm* — Sterne, Kessler, Goldstein & Fox P.L.L.C.

(57) ABSTRACT

Facially amphiphilic polyphenylene and heteroarylene polymers and articles made therform having biocidal surfaces are disclosed. The polymers can inhibit the growth of microorganisms in contact with the surface or in areas adjacent to said biocidal surface. There is also disclosed a methods to attach facially amphiphilic polmers to a solid support. Utility as a contact disinfectant is disclosed.

27 Claims, 3 Drawing Sheets

(56) References Cited

U.S. PATENT DOCUMENTS

| | | | |
|---|---|---|---|
| 5,520,910 A | 5/1996 | Hashimoto | |
| 5,543,448 A | 8/1996 | Laughner | |
| 5,648,070 A | 7/1997 | Brian, III et al. | |
| 5,847,047 A | 12/1998 | Haynie | |
| 5,856,245 A | 1/1999 | Caldwell et al. | |
| 5,874,164 A | 2/1999 | Caldwell | |
| 5,912,116 A | 6/1999 | Caldwell | |
| 5,967,714 A | 10/1999 | Ottersbach et al. | |
| 5,989,295 A | 11/1999 | de la Mettrie et al. | |
| 5,994,340 A | 11/1999 | Maiti et al. | |
| 6,034,129 A | 3/2000 | Mandeville, III et al. | |
| 6,040,251 A | 3/2000 | Caldwell | |
| 6,083,602 A | 7/2000 | Caldwell et al. | |
| 6,107,397 A | 8/2000 | Blankenburg et al. | |
| 6,121,255 A | 9/2000 | Hwu et al. | |
| 6,166,172 A | 12/2000 | McCullough et al. | |
| 6,290,973 B1 | 9/2001 | Hawkins et al. | |
| 6,309,633 B1 | 10/2001 | Ekwuribe et al. | |
| 6,399,629 B1 | 6/2002 | Chamberland et al. | |
| 6,537,961 B1 | 3/2003 | Koch | |
| 6,552,142 B1 | 4/2003 | Meffert et al. | |
| 6,686,345 B2 | 2/2004 | Kerwin et al. | |
| 6,878,387 B1 | 4/2005 | Petereit et al. | |
| 7,173,102 B2 | 2/2007 | DeGrado et al. | |
| 7,332,623 B2 | 2/2008 | Wu et al. | |
| 7,378,479 B2 | 5/2008 | Tamareselvy et al. | |
| 7,465,820 B2 | 12/2008 | Cunsolo et al. | |
| 7,553,876 B2 | 6/2009 | Shaker | |
| 7,590,517 B2 | 9/2009 | Doerksen et al. | |
| 7,745,662 B2 | 6/2010 | Shaker | |
| 7,781,498 B2 | 8/2010 | Krishnan | |
| 8,129,566 B2 | 3/2012 | Mousa et al. | |
| 8,222,456 B2 | 7/2012 | DeGrado et al. | |
| 8,232,428 B2 | 7/2012 | Mousa et al. | |
| 8,236,800 B2 | 8/2012 | DeGrado et al. | |
| 8,455,490 B2 | 6/2013 | DeGrado et al. | |
| 8,507,723 B2 | 8/2013 | Mousa et al. | |
| 8,716,530 B2 | 5/2014 | DeGrado et al. | |
| 2001/0044459 A1 | 11/2001 | Jackson et al. | |
| 2002/0132797 A1 | 9/2002 | Kerwin et al. | |
| 2003/0130454 A1 | 7/2003 | Seya et al. | |
| 2004/0102941 A1 | 5/2004 | Lopez et al. | |
| 2004/0185257 A1 | 9/2004 | DeGrado et al. | |
| 2005/0004211 A1 | 1/2005 | Wu et al. | |
| 2005/0287108 A1 | 12/2005 | DeGrado et al. | |
| 2006/0024264 A1 | 2/2006 | Kuroda et al. | |
| 2006/0041023 A1 | 2/2006 | DeGrado et al. | |
| 2006/0041024 A1 | 2/2006 | Shaker | |
| 2006/0241052 A1 | 10/2006 | DeGrado et al. | |
| 2007/0173752 A1 | 7/2007 | Schonfeldt | |
| 2008/0176807 A1 | 7/2008 | DeGrado et al. | |
| 2012/0202887 A1 | 8/2012 | DeGrado et al. | |

FOREIGN PATENT DOCUMENTS

| | | |
|---|---|---|
| CN | 1335303 A | 2/2002 |
| EP | 0 230 539 A2 | 8/1987 |
| GB | 1 324 087 A | 7/1973 |
| GB | 1 566 512 A | 4/1980 |
| GB | 2 188 585 A | 10/1987 |
| JP | 52-034935 A | 3/1977 |
| JP | 52-085133 A | 7/1977 |
| JP | 56-123903 A | 9/1981 |
| JP | 59-177558 U | 11/1984 |
| JP | 63-108019 A | 5/1988 |
| JP | 7-2808 A | 1/1995 |
| JP | 10-505592 T | 6/1998 |
| JP | 11-152329 A | 6/1999 |
| JP | 2001-133975 A | 5/2001 |
| JP | 2002-363261 A | 12/2002 |
| JP | 2003-165805 A | 6/2003 |
| JP | 2004-168802 A | 6/2004 |
| JP | 2004-323688 A | 11/2004 |
| JP | 2005-507953 A | 3/2005 |
| JP | 2007-516741 | 6/2007 |
| WO | WO 87/01591 A2 | 3/1987 |
| WO | WO 93/14146 A1 | 7/1993 |
| WO | WO 95/19974 A2 | 7/1995 |
| WO | WO 96/09285 A1 | 3/1996 |
| WO | WO 97/29160 | 8/1997 |
| WO | WO 97/49413 | 12/1997 |
| WO | WO 99/48461 A2 | 9/1999 |
| WO | WO 00/37541 A1 | 6/2000 |
| WO | WO 00/44348 A2 | 8/2000 |
| WO | WO 00/69937 A1 | 11/2000 |
| WO | WO 01/51456 A2 | 7/2001 |
| WO | WO 01/55085 A1 | 8/2001 |
| WO | WO 01/72715 A2 | 10/2001 |
| WO | WO 02/072007 A2 | 9/2002 |
| WO | WO 02/095044 A2 | 11/2002 |
| WO | WO 02/100295 A2 | 12/2002 |
| WO | WO 03/009807 A2 | 2/2003 |
| WO | WO 2004/014903 A1 | 2/2004 |
| WO | WO 2004/026958 A1 | 4/2004 |
| WO | WO 2004/082634 A2 | 9/2004 |
| WO | WO 2005/028422 A1 | 3/2005 |
| WO | WO 2005/072246 A2 | 8/2005 |
| WO | WO 2005/123660 A2 | 12/2005 |
| WO | WO 2006/042104 A2 | 4/2006 |
| WO | WO 2006/093813 A2 | 9/2006 |
| WO | WO 2006/132647 A2 | 12/2006 |

OTHER PUBLICATIONS

Bunz, U.H.F., et al., "Poly(arylenethynylenes: Synthesis, Properties, Structures, and Applications", 2000, Chem Rev., 100, pp. 1605-1644.*

Weder, C., et al., "Effect of the Solid State Structure . . . ", 1996, J. Phys., Chem., 100, pp. 18931-18936.*

Dialog File 351, Accession No. 11931138, English language abstract of WO 98/17625 A1.

Dialog File 351, Accession No. 5092300, English language abstract for JP 2-29436 A.

Dialog File 351, Accession No. 6881217, English language abstract for JP 63-22067 A.

Co-pending U.S. Appl. No. 11/361,050, DeGrado, W., et al., filed Feb. 24, 2006 (Not Published).

Appella, D.H., et al., "Formation of Short, Stable Helices in Aqueous Solution by β-Amino Acid Hexamers," J. Am. Chem. Soc. 121:2309-2310, American Chemical Society (1999).

Arnt, L., and Tew, G.N., "New Poly(phenyleneethynylene)s with Cationic, Facially Amphiphilic Structures," J. Am. Chem. Soc. 124:7664-7665, American Chemical Society (Jun. 2002).

Arnt, L., and Tew, G.N., "Phenylene Ethynylene Polymers with Amphiphilic Structures," Polymer Prepr. 43:445, American Chemical Society (Fall 2002).

Barron, A.E., and Zuckerman, R.N., "Bioinspired polymeric materials: in-between proteins and plastics," Curr. Opin. Chem. Biol. 3:681-687, Current Biology Ltd. (1999).

Berresheim, A.J., et al., "Polyphenylene Nanostructures," Chem. Rev. 99:1747-1785, American Chemical Society (1999).

Bjørnholm, T., et al., "Self-Assembly of Regioregular, Amphiphilic Polythiophenes into Highly Ordered π-Stacked Conjugated Polymer Thin Films and Nanocircuits," J. Am. Chem. Soc. 120:7643-7644, American Chemical Society (1998).

Boman, H.G., "Innate immunity and the normal microflora," Immunol. Rev. 173:5-16, Munksgaard International Publishers (Feb. 2000).

Brooks, B.R., et al., "CHARMM: A Program for Macromolecular Energy, Minimization, and Dynamics Calculations," J. Comp. Chem. 4:187-217, John Wiley & Sons (1983).

Calzia, K.J., and Tew, G.N., "Copolymers Containing Metal Binding Ligands for use in Supramolecular Materials: Toward Metal Induced reversible Networks," Polymer Prepr. 43:408-409, American Chemical Society (Fall 2002).

Car, R., and Parrinello, M., "Unified Approach for Molecular Dynamics and Density-Functional Theory," Phys. Rev. Lett. 55:2471-2474, American Physical Society (1985).

Chen, J., et al., "Development of Protegrins for the Treatment and Prevention of Oral Mucositis: Structure-Activity Relationships of

(56) References Cited

OTHER PUBLICATIONS

Synthetic Protegrin Analogues," *Biopolymers* 55:88-98, Wiley Interscience (2000) (Published online Jul. 28, 2000).
Gellman, S.H., "Foldamers: A Manifesto," *Acc. Chem. Res.* 31:173-180, American Chemical Society (1998).
Gennaro, R., and Zanetti, M., "Structural Features and Biological Activities of the Cathelicidin-Derived Antimicrobial Peptides," *Biopolymers* 55:31-49, Wiley Interscience (2000) (Published online Jul. 28, 2000).
Hancock, R.E.W., and Lehrer, R., "Cationic peptides: a new source of antibiotics," *Trends Biotechnol.* 16:82-88, Elsevier Science Publishers B.V. (1998).
Haynie, S.L., et al., "Antimicrobial Activities of Amphiphilic Peptides Covalently Bonded to a Water-Insoluble Resin," *Antimicrob. Agents Chemother.* 39:301-307, American Society for Microbiology (1995).
Houseman, B.T., and Mrksich, M., "The microenvironment of immobilized Arg-Gly-Asp peptides is an important determinant of cell adhesion," *Biomaterials* 22:943-955, Elsevier Science (May 2001).
Hsu, S-H., and Chen, W-C., "Improved cell adhesion by plasma-induced grafting of L-lactide onto polyurethane surface," *Biomaterials* 21:359-367, Elsevier Science (Feb. 2000).
Kelly, T.J., et al., "Emission Rates of Formaldehyde from Materials and Consumer Products Found in California Homes," *Environ. Sci. Technol.* 33:81-88, American Chemical Society (1999).
Kim, J., and Swager, T.M., "Control of conformational and interpolymer effects in conjugated polymers," *Nature* 411:1030-1034, Nature Publishing Group (Jun. 2001).
Kim, J., et al., "Structural Control in Thin Layers of Poly(p-phenyleneethynylene)s: Photophysical Studies of Langmuir and Langmuir-Blodgett Films," *J. Am. Chem. Soc.* 124:7710-7718, American Chemical Society (Jul. 2002) (Published online Jun. 8, 2002).
Klok, H-A., et al., "Self-Assembling Biomaterials," *Polymer Prepr.* 39:166-167, American Chemical Society (1998).
Kochendoerfer, G.G., et al., "Total Chemical Synthesis of the Integral Membrane Protein Influenza A Virus M2: Role of Its C-Terminal Domain in Tetramer Assembly," *Biochemistry* 38:11905-11913, American Chemical Society (1999).
Margel, S., et al., "Peptide, protein, and cellular interactions with self-assembled monolayer model surfaces," *J. Biomed. Mater. Res.* 27:1463-1476, Wiley Interscience (1993).
Martin, M.G., and Siepmann, J.I., "Novel Configurational-Bias Monte Carlo Method for Branched Molecules. Transferable Potentials for Phase Equilibria. 2. United-Atom Description of Branched Alkanes," *J. Phys. Chem. B* 103:4508-4517, American Chemical Society (1999).
Massia, S.P., and Hubbell, J.A., "An RGD Spacing of 440 nm Is Sufficient for Integrin $\alpha_v\beta_3$-mediated Fibroblast Spreading and 140 nm for Focal Contact and Stress Fiber Formation," *J. Cell Biol.* 114:1089-1100, Rockefeller University Press (1991).
Massia, S.P., and Hubbell, J.A., "Covalent Surface Immobilization of Arg-Gly-Asp- and Tyr-Ile-Gly-Ser-Arg-Containing Peptides to Obtain Well-Defined Cell-Adhesive Substrates," *Anal. Biochem.* 187:292-301, Academic Press (1990).
Massia, S.P., and Stark, J., "Immobilized RGD peptides on surface-grafted dextran promote biospecific cell attachment," *J. Biomed. Mater. Res.* 56:390-399, Wiley Interscience (2001) (Published online May 14, 2001).
Mrksich, M., "Tailored substrates for studies of attached cell culture," *Cell. Mol. Life Sci.* 54:653-662, Birkhauser Verlag (1998).
Mrksich, M., and Whitesides, G.M., "Using Self-Assembled Monolayers to Understand the Interactions of Man-Made Surfaces with Proteins and Cells," *Annu. Rev. Biophys. Biomol. Struct.* 25:55-78, Annual Reviews (1996).
Muir, T.W., et al., "Protein Synthesis by Chemical Ligation of Unprotected Peptides in Aqueous Solution," *Methods Enzymol.* 289:266-298, Academic Press (1997).

Nelson, J.C., et al., "Solvophobically Driven Folding of Nonbiological Oligomers," *Science* 277:1793-1796, American Association for the Advancement of Science (1997).
Oren, Z., and Shai, Y., "Mode of Action of Linear Amphipathic $\alpha$-Helical Antimicrobial Peptides," *Biopolymers* 47:451-463, Wiley Interscience (1998).
Piskin, E., "Plasma processing of biomaterials," *J. Biomater. Sci. Polymer Edn.* 4:45-60, VSP (1992).
Pralle, M.U., et al., "Self Assembled Phenylene Vinylene Materials," *Microsc. Microanal.* 8(Suppl. 2):318, Fig. 1, Cambridge University Press (Aug. 2002).
Prince, R.B., et al., "Cooperative Conformational Transitions in Phenylene Ethynylene Oligomers: Chain-Length Dependence," *J. Am. Chem. Soc.* 121:3114-3121, American Chemical Society (1999).
Prince, R.B., et al., "Twist Sense Bias Induced by Chiral Side Chains in Helically Folded Oligomers," *Angew. Chem. Int. Ed.* 39:228-230, Academic Press (Jan. 2000).
Röthlisberger, U., et al., "The torsional potential of perfluoro n-alkanes: A density functional study," *J. Chem. Phys.* 104:3692-3700, American Institute of Physics (1996).
Scherf, U., "Oligo- and Polyarylenes, Oligo- and Polyarylenevinylenes," *Top. Curr. Chem.* 201:163-222, Springer-Verlag (1999).
Seebach, D, and Matthews, J.L., "β-Peptides: a surprise at every turn," *Chem. Commun.* 21:2015-2022, Chemical Society (1997).
Sekaran, G., et al., "Physicochemical and Thermal Properties of Phenol-Formaldehyde-Modified Polyphenol Impregnate," *J. Applied Polymer Sci.* 81:1567-1571, Wiley (Aug. 2001) (Published online May 30, 2001).
Siepmann, J.J., and Frenkel, D., "Configurational bias Monte Carlo: a new sampling scheme for flexible chains," *Mol. Phys.* 75:59-70, Taylor & Francis Ltd. (1992).
Sondossi, M., et al., "Factors Involved in Bactericidal Activities of Formaldehyde and Formaldehyde Condensate/Isothiazolone Mixtures," *Int. Biodeter. Biodegradation* 32:243-261, Elsevier Science (1993).
Stigers, K.D., et al., "Designed molecules that fold to mimic protein secondary structures," *Curr. Opin. Chem. Biol.* 3:714-723, Current Biology Ltd. (1999).
Stupp, S.I., et al., "Functionalized Supramolecular Materials," *Polymer* 39:4505-4508, Elsevier Science (1998).
Tew, G.N., and Stupp S.I., "Multifunctional Supramolecular Materials," *ACS Symp. Ser.* 704:218-226, American Chemical Society (1998).
Tew, G.N., et al., "De novo design of biomimetic antimicrobial polymers," *Proc. Natl. Acad. Sci. USA* 99:5110-5114, National Academy of Sciences (Apr. 2002).
Tew, G.N., et al., "Simple Facially Amphiphilic Polymers as Peptide Mimics," *224th ACS National Meeting*, Boston, MA, Aug. 18-22, 2002, Abstract 4, American Chemical Society (Aug. 2002).
Tew, G.N., et al., "Supramolecular Materials with Electroactive Chemical Functions," *Angew. Chem. Int. Ed.* 39:517-521, Wiley-VCH (Feb. 2000).
Tiller, J.C., et al., "Designing surfaces that kill bacteria on contact," *Proc. Natl. Acad. Sci. USA* 98:5981-5985, National Academy of Sciences (May 2001).
Vlugt, T.J.H., et al., "Improving the efficiency of the configurational-bias Monte Carlo algorithm," *Mol. Phys.* 94:727-733, Taylor & Francis Ltd. (1998).
Wick, C.D., et al., "Transferable Potentials for Phase Equilibria. 4. United-Atom Description of Linear and Branched Alkenes and Alkylbenzenes," *J. Phys. Chem. B* 104:8008-8016, American Institute of Physics (Aug. 2000).
Woo, G.L.Y., et al., "Synthesis and characterization of a novel biodegradable antimicrobial polymer," *Biomaterials* 21:1235-1246, Elsevier Science (Jun. 2000).
U.S. Appl. No. 10/471,028, DeGrado et al., U.S. National Phase of International Appl. No. PCT/US02/22043, filed Mar. 7, 2002, published as WIPO Publication No. WO 02/100295 on Dec. 19, 2002.
U.S. Appl. No. 10/801,951, DeGrado et al., filed Mar. 17, 2004 (Not Published).

(56) References Cited

OTHER PUBLICATIONS

U.S. Appl. No. 10/446,171, Doerksen et al., filed May 28, 2003.
Braga, D., and Grepioni, F., "Making crystals from crystals: a green route to crystal engineering and polymorphism," *Chem. Commun.* 29:3635-3645, The Royal Society of Chemistry (Aug. 2005).
Chattaway, F.D., and Evans, R.C. T., "LXXI.—*The Diphenylbenzens*. I. *Metadiphenylbenzene*," *J. Chem. Soc. Trans.* 69:980-985, Chemical Society (1896).
Hamuro, Y., et al., "De Novo Design of Antibacterial β-Peptides," *J. Am. Chem. Soc.* 121:12200-12201, American Chemical Society (1999).
Dialog File 351, Accession No. 9060205, English language abstract for CN 1181926A.
Dialog File 351, Accession No. 9688439, English language abstract for CN 1270625A.
Office Action mailed on Feb. 5, 2009 in U.S. Appl. No. 11/361,050, inventors DeGrado et al., filed Feb. 24, 2006.
Office Action mailed on Mar. 29, 2007 in U.S. Appl. No. 10/801,951, inventors DeGrado et al., filed Mar. 17, 2004.
Office Action mailed on Oct. 30, 2007 in U.S. Appl. No. 10/801,951, inventors DeGrado et al., filed Mar. 17, 2004.
Office Action mailed on Jul. 28, 2008 in U.S. Appl. No. 10/801,951, inventors DeGrado et al., filed Mar. 17, 2004.
Office Action mailed on Feb. 2, 2009 in U.S. Appl. No. 10/801,951, inventors DeGrado et al., filed Mar. 17, 2004.
Office Action mailed on May 21, 2009 in U.S. Appl. No. 11/038,787, inventors DeGrado et al., filed Jan. 21, 2005.
Office Action mailed on May 8, 2006 in U.S. Appl. No. 10/471,028, inventors DeGrado et al., filed May 11, 2004.
Office Action mailed on Oct. 11, 2005 in U.S. Appl. No. 10/471,028, inventors DeGrado et al., filed May 11, 2004.
Office Action mailed on Nov. 9, 2011 in U.S. Appl. No. 11/038,787, inventors DeGrado, W., et al., filed Jan. 21, 2005, 9 pages.
Office Action mailed on Nov. 10, 2011, in U.S. Appl. No. 11/980,785, inventors DeGrado, W., et al., filed Oct. 31, 2007, 52 pages.
Andersen, J., et al., "Lactoferrin and Cyclic Lactoferricin Inhibit the Entry of Human Cytomegalovirus into Human Fibroblasts," *Antiviral Res.* 51:141-149, Elsevier Science B.V., Netherlands (2001).
Arnt, L., et al. "Nonhemolytic Abiogenic Polymers as Antimicrobial Peptides Mimics," *J. Polym. Sci. A Polym. Chem.* 42:3860-3864, John Wiley and Sons, United States (2004).
Arnt, L., et al., "Amphiphilic Secondary Structure in Phenylene Ethynylenes," *Polymer Preprints* 44:1266-1267, Division of Polymer Chemistry, Inc., American Chemical Society, United States (2003).
Atwell, G., et al., "Synthesis, DNA interactions and biological activity of DNA minor groove targeted polybenzamide-linked nitrogen mustards," *Bioorg. Med. Chem.* 3:679-691, Elsevier Science Ltd., United Kingdom (1995).
Baker, M., et al., "Anticancer Efficacy of Magainin2 and Analogue Peptides," *Cancer Res.* 53:3052-3057, American Association for Cancer Research, Inc., United States (1993).
Barany, G., et al., "Solid-Phase Peptide Synthesis: A Silver Anniversary Report," *Int. J. Pept. Protein Res.* 30:705-739, Munksgaard International Publishers Ltd., Denmark (1987).
Bastian, A. and Schäfer, H., "Human α-Defensin 1 (HNP-1) Inhibits Adenoviral Infection in Vitro," *Regul. Pept.* 101:157-161, Elsevier Science, B.V., Netherlands (2001).
Belaid, A., et al., "In Vitro Antiviral Activity of Dermaseptins Against Herpes Simplex Virus Type 1," *J. Med. Virol.* 66:229-234, Wiley-Liss, Inc., United States (2002).
Boman, H., et al., "Cell-Free Immunity in Cecropia. A Model System for Antibacterial Proteins," *Eur. J. Biochem.* 201:23-31, Springer International, United Kingdom (1991).
Borsche, W., "Über die Reaktionsfähigkeit der Seitenketten in den kernnitrierten Homologen des Benzols," in *Justus Liebig's Annalen Der Chemie*, vol. 386, pp. 351-373, C.F. Winter'sche Verlagshandlung, Germany (1912).
Bradley, J. and Scheld, W., "The Challenge of Penicillin-Resistant *Streptococcus pneumoniae* Meningitis: Current Antibiotic Therapy in the 1990s," *Clin. Infect. Dis.* 24 (Suppl. 2):S213-S221, University of Chicago Press, United States (1997).
Breitenkamp, R. and Tew, G., "Aggregation Studies of Novel, Facially Amphiphilic Phenylene Ethynylenes," *Polymer Preprints* 44:673-674, Division of Polymer Chemistry, Inc., American Chemical Society, United States (2003).
Broekaert, W., et al., "An Automated Quantitative Assay for Fungal Growth Inhibition," *FEMS Microbiol. Lett.* 69:55-59, Elsevier, The Netherlands (1990).
Butler, J., et al., "The Continued Emergence of Drug-Resistant *Streptococcus pneumoniae* in the United States: An Update from the Centers of Disease Control and Prevention's Pneuomococcal Sentinel Surveillance System," *J. Infect. Dis.* 174:986-993, University of Chicago Press, United States (1996).
Chapman, R., et al., "Small molecule modulators of HIV Rev/Rev response element interaction identified by random screening," *Antiviral Res.* 54:149-162, Elsevier, Netherlands (2002).
Cole, A., et al., "Retrocyclin: A Primate Peptide that Protects Cells From Infection by T- and M-tropic Strains of HIV-1," *Proc. Natl. Acad. Sci USA* 99:1813-1818, The National Academy of Sciences, United States (2002).
Cruciani, R., et al., "Antibiotic Magainins Exert Cytoloytic Activity Against Tranformed Cell Lines Through Channel Formation," *Proc. Natl. Acad. Sci. USA* 88:3792-3796, The National Academy of Sciences, United States (1991).
Debono, M. and Gordee, R., "Antibiotics that Inhibit Fungal Cell Wall Development," *Annu. Rev. Microbiol.* 48:471-497, Annual Reviews Inc., United States (1994).
Decosterd, L. et al., "High-performance liquid chromatography of the renal blood flow marker *p*-aminohippuric acid (PAH) and its metabolite N-acetyl PAH improves PAH clearance measurements." *J. Chromatogr. B.* 703:25-36, Elsevier, Netherlands (1997).
DeGrado, W., "Design of Peptides and Proteins," *Adv. Prot. Chem.* 39:51-124, Academic Press Limited, United Kingdom (1988).
DeGrado, W., et al., "Design, Synthesis and Characterization of a Cytotoxic Peptide with Melittin-Like Activity," *J. Amer. Chem. Soc.* 103:679-681, American Chemical Society, United States (1981).
DeGrado, W., et al., "Kinetics and Mechanism of Hemolysis Induced by Melittin and by a Synthetic Melittin Analogue," *Biophys J.* 37:329-338, The Rockefeller University Press, United States (1982).
De Lucca, A. and Walsh, T., "Antifungal Peptides: Novel Therapeutic Compounds Against Emerging Pathogens," *Antimicrob. Agents Chemother.* 43:1-11, American Society for Microbiology, United States (1999).
Dempsey, C., "The Actions of Melittin on Membranes," *Biochim. Biophys. Acta* 1031:143-161, Elsevier Science B.V. , Netherlands (1990).
Dermer, G., "Another Anniversary for the War on Cancer," *Bio/Technology* 12:320, Nature Publishing Group, United Kingdom (1994).
Diness, V. and Østergaard, P., "Neutralization of a Low Molecular Weight Heparin (LHN-1) and Conventional Heparin by Protamine Sulfate in Rats," *Thromb. Haemost.* 56:318-322, F.K. Schattauer Verlag GmbH, Germany (1986).
Edwards, J., et al., "In Vitro Antibacterial Activity of SM-7338, a Carbapenem Antibiotic with Stability to Dehydropeptidase I," *Antimicrob. Agents Chemother.* 33:215-222, American Society for Microbiology, United States (1989).
Egal, M., et al., "Antiviral Effects of Synthetic Membrane-Active Peptides on Herpes Simplex Virus, Type 1," *Int. J. Antimicrob. Agents* 13:57-60, Elsevier Science B.V., Netherlands (1999).
Freshney, R., "Culture of Animal Cells: A manual of basic technique," Liss, A., ed., pp. 4, Wiley-Liss, New York, United States (1983).
Ganz, T., et al., "Defensins," *Eur. J. Haematol.* 44:1-8, Munksgaard International Publishers Ltd., Denmark (1990).
Ganz, T., et al., "Defensins. Natural Peptide Antibiotics of Human Neutrophils," *J. Clin. Invest* 76:1427-1435, The American Society for Clinical Investigation, Inc., United States (1985).
Gazit, E., et al., "Interaction of the Mammalian Antibacterial Peptide Cecropin P1 with Phospholipid Vesicles," *Biochemistry* 34:11479-11488, American Chemical Society, United States (1995).

(56) References Cited

OTHER PUBLICATIONS

Guillemot, D., et al., "Low Dosage and Long Treatment Duration of β-Lactam," *JAMA* 279:365-370, American Medical Association, United States (1998).
Gura, T., "Systems for Identifying New Drugs Are Often Faulty," *Science* 278:1041-42, American Association for the Advancement of Science, United States (1997).
Hamuro, Y., et al., "Novel Folding Patterns in a Family of Oligoanthranilamides: Non-Peptide Oligomers That Form Extended Helical Secondary Structures," *J. Am. Chem. Soc.* 119:10587-10593, American Chemical Society, United States (1997).
Haugwitz, R., et al., "Antiparisitic agents. 6. Synthesis and anthelmintic activities of novel isothiocyanatophenyl-1,2,4-oxadiazoles," *J. Med. Chem.* 28:1234-1241, American Chemical Society, United States (1985).
Hiramatsu, K., et al., "Methicilin-resistant *Staphylococcus aureus* clinical strain with reduced vancomycin susceptibility," *J. Antimicrob. Chemother.* 40:135-136, The British Society for Antimicrobial Chemotherapy, United Kingdom (1997).
Hirsh, J. and Levine, M., "Low Molecular Weight Heparin," *Blood* 79:1-17, The American Society of Hematology, United States (1992).
Hwu, J., et al., "Cephalosporin 3'-Phloroglucide Esters and 7-(Phloroglucidamido) cephalosporins as Novel Antibacterial Agents," *J. Med. Chem.* 40:3434-3441, American Chemical Society, United States (1997).
Javadapour, M., et al., "De Novo Antimicrobial Peptides with Low Mammalian Cell Toxicity," *J. Med. Chem.* 39:3107-3113, American Chemical Society, United States (1996).
Kandrotas, R., "Heparin Pharmocokinetics and Pharmacodynamics," *Clin. Pharmacokinet.* 22:359-374, Adis International Ltd., New Zealand (1992).
Landon, C., et al., "Solution Structure of Drosomycin, the First Inducible Antifungal Protein From Insects," *Protein Sci.* 6:1878-1884, Cambridge University Press, United Kingdom (1997).
Lathers, C., "Clinical Pharmacology of Antimicrobial Use in Humans and Animals," *J. Clin. Pharmacol.* 42:587-600, Sage Science Press, United States (2002).
Liu, D. and DeGrado, W., "De Novo Design, Synthesis, and Characterization of Antimicrobial β-Peptides," *J. Amer. Chem. Soc.* 123:7553-7559, American Chemical Society, United States (2001).
Liu, D., et al., "Nontoxic Membrane-Active Antimicrobial Arylamide Oligomers," *Angew. Chem. Int. Ed. Engl.* 43:1158-1162, Verlag Chemie, Germany (2004).
Lyytikäinen, O., et al., "Outbreak caused by two multi-resistant *Acinetobacter baumannii* clones in a burns unit: emergence of resistance to imipenem," *J. Hosp. Infect.* 31:41-54, W.B. Saunders Company Ltd., United Kingdom (1995).
Maloy, W. and Kari, U., "Structure-Activity Studies on Magainins and Other Host Defense Peptides," *Biopolymers* 37:105-122, John Wiley & Sons, Inc., United States (1995).
Markovak, A., and LaMontagne, M., "Antimalarials. 12. Preparation of Carbon Isosteres of Selected 4-Pyridinemethanols as Suppressive Antimalarials," *J. Med. Chem.* 23:1198-1201, American Chemical Society, United States (1980).
Merrifield, E., et al., "D-Enantiomers of 15-Residue Cecropin A-Melittin Hybrids," *Int. J. Pept. Protein Res.* 46:214-220, Munksgaard, Belgium (1995).
Merrifield, R., et al., "Design and Synthesis of Antimicrobial Peptides," *Ciba Found. Symp.* 186:5-26, John Wiley & Sons Ltd., United Kingdom (1994).
Merrifield, R., et al., "Retro and Retroenantio Analogs of Cecropin-Melittin Hybrids," *Proc. Natl. Acad. Sci. USA* 92:3449-3453, National Academy of Sciences, United States (1995).
Monroe, S. and Polk, R., "Antimicrobial use and bacterial resistance," *Curr. Opin. Microbiol.* 3:496-501, Elsevier Science Ltd., Netherlands (2000).
Montecalvo, M., et al., "Outbreak of Vancomycin-, Ampicillin-, and Aminoglycoside-Resistant *Enterococcus faecium* Bacteremia in an Adult Oncology Unit," *Antimicro. Agents Chemother.* 38:1363-1367, American Society for Microbiology, United States (1994).

Nicolaus, B., "Symbiotic Approach to Drug Design," in *Decision Making in Drug Research*, pp. 173-186, Gross, F., ed., Raven Press, United States (1983).
Okumura, K., et al., "C-Terminal Domain of Human CAP18 Antimicrobial Peptide Induces Apoptosis in Oral Squamous Cell Carcinoma SAS-H1 cells," *Cancer Lett.* 212:185-194, Elsevier Ireland Ltd., Ireland (2004).
Orita, A., et al., "Double Elimination Protocol for Access to Unsymmetrical Di(phenylethynyl)benzenes," *Chemistry Letters* 32:104-105, The Chemical Society of Japan, Japan (CAPLUS abstract) (2003).
Papo, N. and Shai, Y., "New Lytic Peptides Based on the D,L-Amphipathic Helix Motif Preferentially Kill Tumor Cells Compared to Normal Cells," *Biochemistry* 42:9346-9354, American Chemical Society, United States (2003).
Papo, N., et al., "Suppression of Human Prostate Tumor Growth in Mice by a Cytolytic D-, L-Amino Acid Peptide: Membrane Lysis, Increased Necrosis, and Inhibition of Prostate-Specific Antigen Secretion," *Cancer Res.* 64:5779-5786, The American Association of Cancer Research, United States (2004).
Patch, J. and Barron, A., "Helical Peptoid Mimics of Magainin-2 Amide," *J. Am. Chem. Soc.* 125:12092-12093, American Chemical Society, United States (2003).
Peggion, E., et al., "Confirmation and Interactions of Bioactive Peptides From Insect Venoms: The Bombolitins," *Biopolymers* 43:419-431, John Wiley & Sons, Inc., United States (1997).
Polymedix, "Low Molecular Weight Heparin Antagonist (2003)," accessed at: http://www.polymedix.com/03_03_low-molecular.htm, accessed on Apr. 27, 2007, pp. 1-2, entire document.
Porter, E., et al., "Antibiotics: Non-haemolytic β-amino-acid oligomers," *Nature* 404:565, Nature Publishing Group, United Kingdom (2000).
Porter, E., et al., "Mimicry of Host-Defense Peptides by Unnatural Oligomers: Antimicrobial β-Peptides," *J. Am. Chem. Soc.* 124:7324-7330, American Chemical Society, United States (2002).
Pouny, Y., et al., "Interaction of Antimicrobial Dermaseptin and Its Fluorescently Labeled Analogues with Phospholipid Membranes," *Biochemistry* 31:12416-12423, American Chemical Society, United States (1992).
Ridgway, G., "Treatment of chlamydial genital infection," *J. Antimicrob. Chemother.* 40:311-314, The British Society for Antimicrobial Chemotherapy, United Kingdom (1997).
Rusanov, A., et al., "The use of palladium-catalysed cross-coupling for the synthesis of polymers incorporating vinylene and ethynylene groups," *Russian Chemical Reviews* 66:1053-1068, Russian Academy of Sciences and Turpion Ltd., Russia (1997).
Samson, N., et al., "Relationship Between Synthesis and Mechanical Properties of New Polyurea Materials," *J. Appl. Polym. Sci.* 65:2265-2280, John Wiley & Sons, Inc., United States (1997).
Scherf, U., "Oligo- and polyarylenes, oligo- and polyarylenevinylenes," in *Carbon Rich Compounds II: Macrocyclic Oligoacetylenes and Other Linearly Conjugated Systems, Topics in Current Chemistry*, de Meijere, A., ed. vol. 201, pp. 163-222, Springer-Verlag, Germany (1999).
Seurynck, S., et al., "Design, Synthesis, and Testing of Peptoid-Based Lung Surfactant Protein Mimics," *Biophysical J.* 84:298A, 1450-Pos Board #B705, Biophysical Society, United States (2003).
Shin, S., et al., "Effects of the hinge region of cecropin A (1-8)-magainin 2(1-12), a synthetic antimicrobial peptide, on liposomes, bacterial and tumor cells," *Biochem. Biophys. Acta* 1463: 209-218, Elsevier Science Ltd., Netherlands (2000).
Shortell, D., et al., "Solid-Phase Approaches Toward Cyclic Oligomers," *Tetrahedron* 57:9055-9065, Elsevier Science Ltd., Netherlands (2001).
Sinha, S., et al., "NP-1, A Rabbit α-Defensin, Prevents the Entry and Intercellular Spread of Herpes Simplex Virus Type 2," *Antimicrob. Agents Chemother.* 47:494-500, American Society of Microbiology, United States (2003).
Steiner, H., et al., "Sequence and Specificity of Two Antibacterial Proteins Involved in Insect Immunity," *Nature*, 292:246-248, Nature Publishing Group, United Kingdom (1981).
Stevens, M., Polymer Chemistry: An Introduction, 3rd ed., pp. 409-424, Oxford University Press, New York (1999).

(56) References Cited

OTHER PUBLICATIONS

Tang, Y., et al., "A Cyclic Antimicrobial Peptide Produced in Primate Leukocytes by the Ligation of Two Truncated α-Defensins," *Science* 286:498-502, American Association for the Advancement of Science, United States (1999).
Tecilla, P., et al., "Hydrogen-bonding self-assembly of multichromophore structures," *J. Am. Chem. Soc.* 112:9408-9410, American Chemical Society, United States (1990).
Tew, G., "Amphiphilic Phenylene Ethynylenes," *Polymer Preprints* 44:452, Division of Polymer Chemistry, Inc., American Chemical Society, United States (2003).
Tew, G., et al., "Antimicrobial Activity of an Abiotic Host Defense Peptide Mimic," *Biochim. Biophys. Acta* 1758:1387-1392, Elsevier B.V., Netherlands (2006).
Threlfall, E., et al., "Increasing spectrum of resistance in multiresistant *Salmonella typhimurium*," *Lancet* 347:1053-1054, Lancet Publishing Group, United States (1996).
Tossi, A., et al., "Amphipathic, α-Helical Antimicrobial Peptides," *Biopolymers* 55:4-30, John Wiley & Sons, Inc., United States (2000).
Turpie, A., "Pharmacology of the Low-Molecular-Weight Heparins," *Am. Heart J.* 135:S329-S335, Mosby, Inc., United States (1998).
Turner, P., et al., "Polybenzamide mustards: structure-activity relationships for DNA sequence-specific alkylation," *Anti-Cancer Drug Des.*14:61-70, Oxford University Press, United Kingdom (1999).
Turner, P., et al., "Role of DNA minor groove alkylation and DNA cross-linking in the cytotoxicity of polybenzamide mustards," *Anti-Cancer Drug Des.* 15:245-253, Oxford University Press, United Kingdom (2000).
Ryn-McKenna, J., et al., "Neutralization of Enoxaparine-Induced Bleeding by Protamine Sulfate," *Thromb. Haemost.* 63:271-274, F.K. Shattauer Verlagsgesellschaft mbH, Germany (1990).
Wachinger, M., et al., "Antimicrobial Peptides Melittin and Cecropin Inhibit Replication of Human Immunodeficiency Virus 1 by Supressing Viral Gene Expression," *J. Gen. Virol.* 79:731-740, The Society for General Microbiology, United Kingdom (1998).
Wakefield, T., et al., "A [+18RGD] Protamine Variant for Nontoxic and Effective Reversal of Conventional Heparin and Low-Molecular-Weight Heparin Anticoagulation," *J. Surg. Res.* 63:280-286, Academic Press, Inc., United States (1996).
Wong, P., et al., "Nonpeptide Factor Xa Inhibitors: I. Studies with SF303 and SK549, a New Class of Potent Antithrombotics," *J. Pharmacol. Exp. Thrap.* 292:351-357, American Society for Pharmacology and Experimental Therapeutics, United States (2000).
Yamaguchi, I., et al., "Synthesis of Polyurea Rotaxanes Using a Cyclodextrin Complexes of α, ω-Diamine," *Polym. Bull.* 44:247-253, Springer-Verlag, Germany (2000).
Zasloff, M., "Antibiotic Peptides as Mediators of Innate Immunity," *Curr. Opin. Immunol.* 4:3-7, Current Biology Ltd., United Kingdom (1992).
Zasloff, M., "Antimicrobial Peptides of Multicellular Organisms," *Nature* 415:389-395, Nature Publishing Group, United Kingdom (2002).
Zasloff, M., "Reconstructing one of Nature's Designs," *Trends Pharmacol. Sci.* 21:236-238, Elsevier Science Ltd., Netherlands (2000).
Zhang, L., et al., "Contribution of Human α-Defensin 1, 2, and 3 to the Anti-HIV-1 Activity of CD8 Antiviral Factor," *Science* 298:995-1000, American Association for the Advancement of Science, United States (2002).
Zhao, C., et al., "Identification of a New Member of the Protegrin Family by cDNA Cloning," *FEBS Lett.* 346:285-288, Federation of European Biochemical Societies, Netherlands (1994).
Patent Abstract of Japan, English Language abstract for JP 52-085133 A, Patent & Utility Model Gazette DB, Japanese Patent Office, 2 pages (1977).
Patent Abstract of Japan, English Language abstract for JP 56-123903 A, Patent & Utility Model Gazette DB, Japanese Patent Office, 2 pages (1981).
Patent Abstract of Japan, English Language abstract for JP 59-177558 U, Patent & Utility Model Gazette DB, Japanese Patent Office, 2 pages (1984).
Esp@cenet Database, English language abstract of JP 7-2808 A, espacenet, European Patent Office, 2 pages (1995).
Esp@cenet Database, English language abstract of JP 10-505592 T, espacenet, European Patent Office, 1 page (1998).
Patent Abstract of Japan, English Language abstract for JP 11-152329 A, Patent & Utility Model Gazette DB, Japanese Patent Office, 1 page (1999).
Esp@cenet Database, English language abstract of WO 00/69937 A1, espacenet, European Patent Office, 1 page (2000).
Esp@cenet Database, English language abstract of CN 1335303 A, espacenet, European Patent Office, 1 page (2002).
Patent Abstract of Japan, English Language abstract for JP 2001-133975 A, Patent & Utility Model Gazette DB, Japanese Patent Office, 2 pages (2001).
Patent Abstract of Japan, English Language abstract for JP 2002-363261 A, Patent & Utility Model Gazette DB, Japanese Patent Office, 2 pages (2002).
Patent Abstract of Japan, English Language abstract for JP 2003-165805 A, Patent & Utility Model Gazette DB, Japanese Patent Office, 2 pages (2003).
Patent Abstract of Japan, English Language abstract for JP 2004-168802 A, Patent & Utility Model Gazette DB, Japanese Patent Office, 2 pages (2004).
Patent Abstract of Japan, English Language abstract for JP 2004-323688 A, Patent & Utility Model Gazette DB, Japanese Patent Office, 2 pages (2004).
Database CAplus on STN, Acc. No. 1912:7297, Borsche, Justus Liebigs Annalen der Chemie (1912), 386, pp. 351-373 (form: Part of Paper No. 20091016).
CAS Registry No. 495410-77-0; Entry date: Feb. 27, 2003.
CAS Registry No. 87774-34-3; Entry date: Nov. 16, 1984.
CAS Registry No. 92-06-8; Entry date: Nov. 16, 1984.
Office Action mailed on Oct. 20, 2009 in U.S. Appl. No. 11/038,787, inventors DeGrado, W., et al., filed Jan. 21, 2005.
Office Action mailed on Jan. 12, 2010 in U.S. Appl. No. 11/038,787, inventors DeGrado, W., et al., filed Jan. 21, 2005.
Office Action mailed on Oct. 25, 2010 in U.S. Appl. No. 11/038,787, inventors DeGrado, W., et al., filed Jan. 21, 2005.
Supplemental Office Action mailed on Mar. 22, 2010 in U.S. Appl. No. 11/038,787, inventors DeGrado, W., et al., filed Jan. 21, 2005.
Office Action mailed on Jul. 1, 2010 in U.S. Appl. No. 11/038,787, inventors DeGrado, W., et al., filed Jan. 21, 2005.
Advisory Action mailed on May 17, 2011 in U.S. Appl. No. 11/038,787, inventors DeGrado, W., et al., filed Jan. 21, 2005.
Office Action mailed on Feb. 22, 2011 in U.S. Appl. No. 11/038,787, inventors DeGrado, W., et al., filed Jan. 21, 2005.
Advisory Action mailed on Jun. 9, 2009 in U.S. Appl. No. 10/801,951, inventors DeGrado, W., et al., filed Mar. 17, 2004.
Notice of Panel Decision from Pre-Appeal Brief Review mailed on Jun. 23, 2009 in U.S. Appl. No. 10/801,951, inventors DeGrado, W., et al., filed Mar. 17, 2004.
Office Action mailed on Apr. 13, 2010, in U.S. Appl. No. 10/801,951, inventors DeGrado, W., et al., filed Mar. 17, 2004.
Office Action mailed on Aug. 6, 2009 in U.S. Appl. No. 11/361,050, inventors DeGrado, W., et al., filed Feb. 24, 2006.
Office Action mailed on Feb. 24, 2010 in U.S. Appl. No. 11/361,050, inventors DeGrado, W., et al., filed Feb. 24, 2006.
Office Action mailed on Sep. 9, 2010 in U.S. Appl. No. 11/361,050, inventors DeGrado, W., et al., filed Feb. 24, 2006.
Advisory Action mailed on Feb. 14, 2011 in U.S. Appl. No. 11/361,050, inventors DeGrado, W., et al., filed Feb. 24, 2006.
Co-pending U.S. Appl. No. 11/038,787, DeGrado, W., et al., filed Jan. 21, 2005 (now U.S. Patent Appl. No. 2005-0287108 A1).
Co-pending U.S. Appl. No. 11/980,785, DeGrado, W., et al., filed Oct. 31, 2007 (now U.S. Patent Application Pub. No. 2008-0176807 A1).
Ishitsuka, Y., et al., "Amphiphilic poly(phenyleneethynylene)s can mimic antimicrobial peptide membrane disordering effect by membrane insertion," *J. Am. Chem. Soc.*, 128(40):13123-13129, American Chemical Society, United States (2006).

(56) References Cited

OTHER PUBLICATIONS

Pearce, H.L., et al., "Chapter 18: Failure modes in anticancer drug discovery and development," in *Cancer Drug Design and Discovery*, Neidle, S., ed., pp. 424-435, Elsevier Inc., United States (2008).

Pugsley, M.K., et al., "Protamine is a low molecular weight polycationic amine that produces actions on cardiac muscle," *Life Sci.* 72(3):293-305, Elsevier, Netherlands (2002).

Roberts, T.G., et al., "Trends in the Risks and Benefits to Patients With Cancer Participating in Phase 1 Clinical Trials," *JAMA* 292(17):2130-2140, American Medical Association, United States (2004).

Tang, H., et al., "Synthesis of urea oligomers and their antibacterial activity," *Chem. Commun.*, pp. 1537-1539, Royal Society of Chemistry, England (2005).

Ulrich, J. and Stelzer, T., Chapter 4 in Crystallization, Kirk-Othmer Encyclopedia of Chemical Technology, John Wiley & Sons, pp. 1-63, United States (2007).

West, A.R., "Solid State Chemistry and Its Applications," pp. 358 and 365, John Wiley & Sons, India (1989).

Office Action mailed Nov. 28, 2012, in U.S. Appl. No. 13/365,840, inventors DeGrado et al., filed Feb. 3, 2012.

Office Action mailed Apr. 30, 2013, in U.S. Appl. No. 13/365,840, inventors DeGrado et al., filed Feb. 3, 2012.

Notice of Allowance mailed Aug. 7, 2013, in U.S. Appl. No. 13/365,840, inventors DeGrado et al., filed Feb. 3, 2012.

Notice of Allowance mailed Jan. 25, 2013, in U.S. Appl. No. 13/559,065, inventors DeGrado et al., filed Jul. 26, 2012.

Office Action mailed Jun. 17, 2013, in U.S. Appl. No. 11/361,050, inventors DeGrado et al., filed Feb. 24, 2006.

Office Action mailed on Jan. 29, 2014, in U.S. Appl. No. 11/361,050, inventors Degrado et al., filed Feb. 24, 2006.

Office Action mailed Sep. 25, 2013, in U.S. Appl. No. 10/801,951, inventors DeGrado et al., filed Mar. 17, 2004.

Office Action mailed on Feb. 3, 2014, in U.S. Appl. No. 10/801,951, inventors DeGrado, et al., filed Mar. 17, 2004.

Atwell, G. and Cain, B., "Potential Antitumor Agents. 13. Bisquaternary Salts," *J. Med Chem.* 16:673-678, American Chemical Society, United States (1973).

Denny, W., et al., "Potential Antitumor Agents. 36. Quantitative Relationships Between Experimental Antitumor Activity, Toxicity, and Structure for the General Class of 9-Anilinoacridine Antitumor Agents," *J. Med Chem.* 25:276-315, American Chemical Society, United States (1982).

Hudson, J. and Towers, G. "Antiviral properties of acetylenes and thiophenes," *Bioactive Molecules* 7:315-338, Elsevier, Amsterdam (1988).

Hudson, J., et al., "Photoactive antiviral and cytotoxic activities of synthetic thiophenes and their acetylenic derivatives," *Chemosphere* 19:1329-1343, Pergamon Press, Great Britain (1989).

Lin, C., et al., "Cytotoxicities, cell cycle, and caspase evaluations of 1,6-diaryl-3(Z)-hexen-1,5-diynes, 2-(6-aryl-3(Z)-hexen-1,5-diynyl)anilines and their derivatives," *Bioorg. Med. Chem.* 13:3565-3575, Elsevier Ltd., England (2005).

STN Database CAplus, "1,2-bis[2-(2,6-difluorophenyl) ethynyl]-benzene" Registry No. 27286-86-8, entered Nov. 16, 1984.

STN Database CAplus, "2,6-bis(2-phenylethynyl)-phenol" Registry No. 478551-27-8, entered Jan. 9, 2003.

STN Database CAplus, "3,5-bis(2-phenylethynyl)-benzoic acid methyl ester," Registry No. 272128-90-2, entered Jun. 22, 2000.

STN Database CAplus, "1,4-dibromo-2,5-bis[2-(2-bromophenyl)ethynyl]-benzene," Registry No. 625389-87-9, entered Dec. 10, 2003.

STN Database CAplus, "4,4'-(1,2-phenylenedi-2,1-ethynediyl)bis [2,3,5,6-tetrafluoropyridine]," Registry No. 459457-30-8, entered Oct. 7, 2002.

STN Database CAplus, "1,2,4,5-tetrafluoro-3,6-bis[2-(4-fluorophenyl)ethynyl]-benzene" Registry No. 332148-91-1, entered Apr. 24, 2001.

STN Database CAplus, "1,4-bis[2-(2,3,4,5,6-pentafluorophenyl)ethynyl]-benzene" Registry No. 258506-15-9, entered Mar. 8, 2000.

Unverified machine generated English translation of Swiss Patent No. CH 520 657 A, published Mar. 31, 1972.

Unverified machine generated English translation of Swiss Patent No. CH 525 898 A, published Jul. 31, 1972.

Vippagunta, S., et al., "Crystalline solids," *Adv. Drug Deliv. Rev.* 48:3-26, Elsevier Science B.V, Netherlands (2001).

Notice of Allowance mailed Mar. 6, 2012 in U.S. Appl. No. 11/980,785, inventors DeGrado, W., et al., filed Oct. 31, 2007.

Non-Final Office Action mailed Jan. 23, 2012, in U.S. Appl. No. 11/038,787, inventors Degrado, W., et al., filed Jan. 21, 2005.

Notice of Allowance mailed Feb. 21, 2012 in U.S. Appl. No. 11/038,787, inventors DeGrado, W., et al., filed Jan. 21, 2005.

\* cited by examiner

FACIALLY AMPHIPHILIC POLYMERS AS ANTI-INFECTIVE AGENTS

REFERENCE TO PREVIOUS APPLICATIONS

This application claims priority to U.S. Provisional Patent Application Ser. No. 60/274,145 filed Mar. 8, 2001.

GOVERNMENT SUPPORT

This invention was supported in part by funding from the U.S. Government (NSF Grant DMR00-79909) and the U.S. Government may therefore have certain rights in the invention.

FIELD OF THE INVENTION

The present invention relates to the design and synthesis of facially amphiphilic polymeric compounds with microbiocidal properties that can be coated on or incorporated into materials and methods to design the same. The present invention further relates to methods to identify and design facially amphiphilic polymers and methods to prevent or limit microbial growth.

BACKGROUND OF THE INVENTION

Amphiphilic molecules exhibit distinct regions of polar and nonpolar character. These regions can result from substitution of hydrophobic and hydrophilic substituents into specific and distinct regions of conformationally defined molecules. Alternately a conformationally flexible molecule or macromolecule can adopt an ordered structure in which the hydrophobic and hydrophilic substituents on the molecule segregate to different areas or faces of the molecule. Commonly occurring amphiphilic molecules include surfactants, soaps, detergents, peptides, proteins and copolymers. These molecules have the capacity to self-assemble in appropriate solvents or at interfaces to form a variety of amphiphilic structures. The size and shape of these structures varies with the specific composition of the amphiphilic molecule and solvent conditions such as pH, ionic strength and temperature.

Amphiphilic peptides with unique broad-spectrum antimicrobial properties have been isolated from a variety of natural sources including plants, frogs, moths, silk worms, pigs and humans (H. G. Boman *Immunol Rev.* 2000 173:5-16; R. E. Hancock and R. Lehrer, *Trends Biotechnol.* 1998 16:82-88). These compounds include the magainin 1 (1) and dernaseptin S1 (2) isolated from the skin of frogs and the cecropin A (3) isolated from the cecropia moth. These naturally occurring compounds have broad-spectrum antibacterial activity and they do not appear prone to the development of bacterial resistance. These compounds are relatively low molecular weight peptides that have a propensity to adopt α-helical conformation in hydrophobic media or near a hydrophobic surface and as a result are facially amphiphilic (i.e., one-third to two-thirds of the cylinder generated by the helical peptide has hydrophobic side chains while the

GIGKFLHSAGKFGKAFVGEIMKS-$CO_2$H (1)

ALWKTMLKKLGTMALHAGKAALGAAADTISQGTQ-$CO_2$H (2)

KWKLFKKIEKVGQNIRDGIIKAGPAVAVVGQATQIAK-$NH_2$ (3)

RGGRLCYCRRRFCVCVGR-$NH_2$ (4)

remainder has hydrophilic side chains. These hydrophilic side chains are primarily positively-charged at neutral pH. Hydrophobic amino acids compose 40-60% of the total number of residues in most anti-microbial peptides. The selectivity of the amphiphilic peptides (e.g. for bacteria vs. human erythrocytes) depends on the overall hydrophobicity. The biological activity of the compounds depend on the ratio of charged (c) to hydrophobic (h) residues. When the ratio is varied from 1:1 (c:h) to 1:2 (c:h) peptides with more hydrophobic residues tend to be more active toward erythrocyte membranes. The physiochemical properties rather than the presence of particular amino acids or the tertiary structure of the side chains. Related peptides have been isolated from mammals and these anti-microbial peptides have been suggested to be an important component of the innate immune response. (Gennaro, R. et aL *Biopoylmers (Peptide Science)* 2000, 55, 31)

These observations recently have been extended to peptides (β-peptides) comprised of □-amino acids. These non-natural polypeptide mimetics also are capable of adopting stable α-helical and β-sheet structures although the precise geometries of these structure are different form those generated by α-amino acid oligomers. However, appropriate positioning of hydrophobic and hydrophilic residues results in amphiphilic conformations with similar antimicrobial properties. This further confirms the importance of repeating periodicity of hydrophobic and hydrophilic groups vis-á-vis the precise amino acid sequence in producing facial amphiphilic antimicrobial compounds. (D. Seebach and J. L. Matthews, *Chem Commun.* 1997 2105; Hamuro, Y., Schneider, J. P., DeGrado, W. F., *J Am. Chem. Soc.* 1999, 121, 12200-12201; D. H. Appella et al., *J Am. Chem. Soc.*, 1999121, 2309)

Secondary structures other than helices may also give rise to amphiphilic compounds. The protegrins (4) are a related series of anti-microbial peptides. (J. Chen et al., *Biopolymers (Peptide Science)*, 2000 55 88) The presence of a pair of disulfide bonds between $Cys^6$-$Cys^{15}$ and $Cys^8$-$Cys^{13}$ results in a monomeric amphiphilic anti-parallel □-sheet formed by the chain termini and linked by a β-turn. The amphiphilic β-sheet conformation is essential for anti-microbial activity against both gram-positive and gram-negative bacteria.

The data related to anti-microbial peptides suggests that facial amphiphilicity, the alignment of polar (hydrophilic) and nonpolar (hydrophobic) side chains on opposite faces of a secondary structural element formed by the peptide backbone, and not amino acid sequence, any particular secondary/tertiary structure, chirality or receptor specificity is responsible for their biological activity Suitably substituted polymers which lack polyamide linkages also are capable of adopting amphiphilic conformations. Solid phase chemistry technology was utilized to synthesize a class of meta substituted phenylacetylenes that fold into helical structures in appropriate solvents (J. C. Nelson et al., *Science* 1997 277:1793-96; R. B. Prince et al., *Angew. Chem. Int. Ed.* 2000 39:228-231). These molecules contain an all hydrocarbon backbone with ethylene oxide side chains such that when exposed to a polar solvent (acetonitrile), the backbone would collapse to minimize its contact with this polar solvent. As a result of the meta substitution, the preferred folded conformation is helical. This helical folding is attributed to a "solvophobic" energy term; although, the importance of favorable π-π aromatic interactions in the folded state are also likely to be important. Furthermore, addition of a less polar solvent (CHCl$_3$) results in an unfolding of the helical structure demonstrating that this folding is reversible.

Regioregular polythiophenes (5 and 6) have been shown to adopt amphiphilic conformations in highly ordered π-stacked arrays with hydrophobic side chains on one side of the array and hydrophilic side chains on the other side. These polymers form thin films useful in the construction of nanocircuits. (Bjornholm et al., *J Am. Chem. Soc.*, 1998 120, 7643) These materials would be facially amphiphilic as defined herein; however, no biological properties have reported for these compounds.

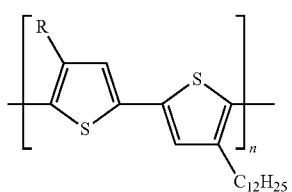

5: R = CH$_2$CO$_2^-$NMe$_4^+$
6: R = (CH$_2$CH$_2$O)$_3$Me

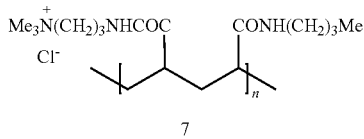

7

Antimicrobial peptides have been incorporated onto surfaces or bulk materials, with some retention of antimicrobial properties. Haynie and co-workers at DuPont have investigated the activity of Antibacterial peptides have been covalently attached to solid surfaces (S. L. Haynie et al., *Antimicrob Agents Chemother*, 1995 39:301-7; S. Margel et al., *J Biomed Mater Res*, 1993, 27:1463-76). A variety of natural and de novo designed peptides were synthesized and tested for activity while still attached to the solid support. The activity of the peptides decreased when attached to the solid support although the peptides retained their broad spectrum of activity. For example, a de novo designed peptide referred to as E14LKK has a MBC (minimum bactericidal activity) of 31 µg/ml in solution as opposed to 1.5 mg/ml when attached to a solid phase bead. The peptides were attached to the resin with a 2 to 6-carbon alkyl linker. The porosity of Pepsyn K, the resin used in the synthesis, is small (0.1 to 0.2 µm) compared to the bacteria, so the microbes may be unable to penetrate into the interior of the resin. Thus the great majority of the peptide would not be available for binding to cells. The antimicrobial activity did not arise from a soluble component; no leached or hydrolyzed peptide was observed and the soluble extracts were inactive. These studies indicate quite convincingly that antimicrobial peptides retain their activity even when attached to a solid support. However, there is a need to optimize the presentation of the peptides to increase their potency.

Other antimicrobial polymeric materials have been reported which contain chemical functionality known to be antimicrobial (J. C. Tiller et al., *Proc Natl Acad Sci USA*, 2001 98:5981-85). A large portion of this work uses chemical functions such as alkylated pyridinium derivatives, which are known to be toxic to mammalian cells. The antibiotic ciprofloxacin has been grafted into a degradable polymer backbone (G. L. Y. Woo; et al., Biomaterials 2000 21:1235-1246). The activity of this material relies on cleavage of the active component from the polymer backbone.

Anti-infective vinyl copolymers, wherein monomers with hydrophobic and hydrophilic side chains have been randomly polymerized to produce polymers with amphiphilic properties, have also been described recently W. H. Mandeville III et al. (U.S. Pat. No. 6,034,129). These materials are produced by polymerization of hydrophobic and hydrophilic acrylate monomers. Alternately, the hydrophobic side chain is derived from a styrene derivative which is copolymerized with a hydrophilic acrylate monomer wherein an ionic group is linked to the carboxylic acid. These polymers, however, have relatively random arrangements of polar and nonpolar groups and are not facially amphiphilic as defined herein.

An alternative method to make amphiphilic polymers is to produce block copolymers comprised of hydrophobic blocks (A) and hydrophilic blocks (B), commonly polypropyleneoxy and polyethylenoxy segments respectively, into A-B, A-B-A or similar copolymers. These copolymers also are not facially amphiphilic as defined herein.

BRIEF DESCRIPTION OF FIGURES

Specific embodiments of the invention have been chosen for the purpose of illustration and description but are not intended in any way to restrict the scope of the invention. These embodiments are shown in the accompanying drawings wherein.

SUMMARY OF THE INVENTION

Figure 1:
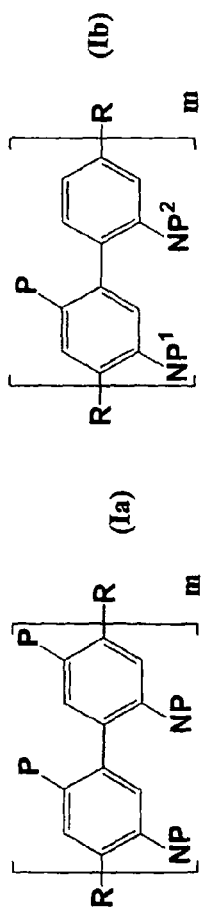
In FIG. 1 there is shown typical examples of two facially amphiphilic p-phenylene monomers, Ia and Ib, and the complete structure of a m-phenylene copolymer Ig.
Figure 1:
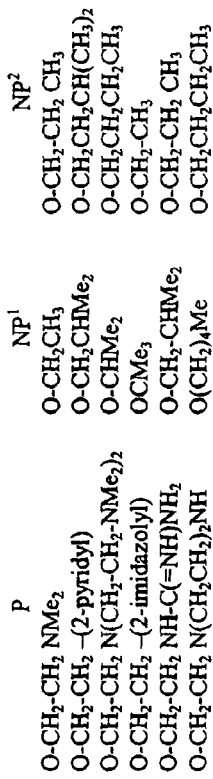
Figure 1:
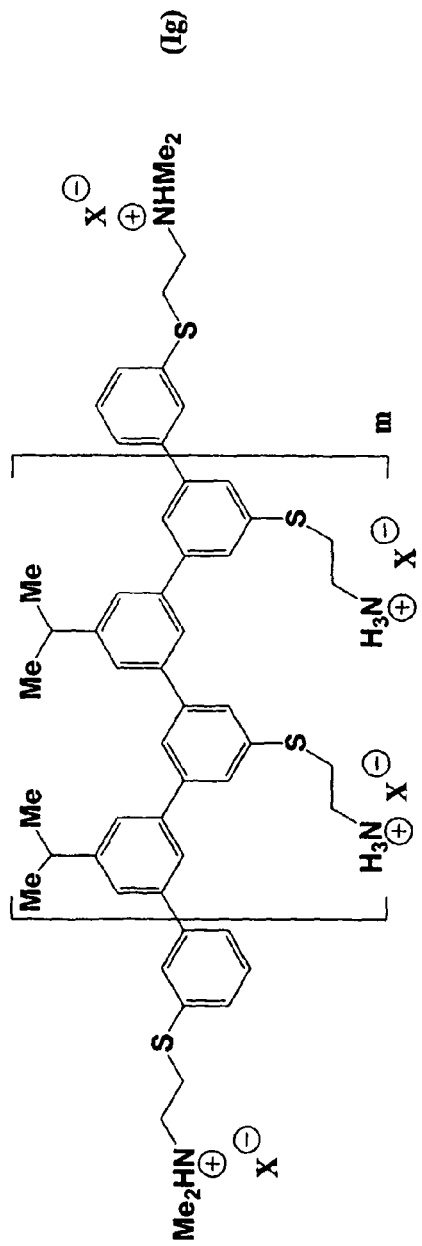

One object of the invention is to provide new polymeric compounds with anti-microbial properties which can be applied to or dispersed throughout devices, articles and surfaces and which are capable of killing microorganisms on contact, but leach into the environment more slowly than traditional small molecule anti-microbials. The polymeric materials may be deposited as a film on the surface of a substrate or may be dispersed

(I)

throughout a substrate to provide an anti-microbial surface. The polymeric materials of the present invention are anti-microbial polymers that are designed to possess amphiphilic properties in the presence of microbial cell walls and to disrupt the membrane and kill the organism. The polymeric materials are further designed to have low toxicity to mammalian cells.

The facially amphiphilic polymers of the present invention are polyphenylene and heteroarylene compounds of formula I wherein is either a single bond, double bond, triple bond or absent and A and B are aromatic, heteroaromatic moieties appropriately substituted with polar and nonpolar groups. R, $R^1$ and $R^2$ are end groups appropriate for the specific polymer chain and their design is well know in the polymer art of formulae These facially amphiphilic polymers are capable of adopting repeating secondary structural motifs that allow for the segregation of polar and nonpolar regions of the molecule into different spatial regions. The anti-microbial polymers adopt amphiphilic conformations when placed in contact with the cell walls of microorganisms and the amphiphilic molecules are capable of disrupting essential cell wall functions resulting in the death of the microorganism.

The present invention further provides methods for killing microorganism on surfaces by disposing thereon a facially amphiphilic polymer. The method for making compositions incorporating the facially amphiphilic polymers includes providing a solution dispersion or suspension of the polymer and applying it to the surface. Alternately compositions can be prepared by incorporating the polymer into plastics that subsequently are molded, shaped or extruded into other articles. The optimal method to deliver the polymer will depend on several factors including the desired coating thickness and the nature and configuration of the substrate and the physical characteristics of the facially amphiphilic polymer.

The facially amphiphilic polymers of the present invention can have a substantial range in molecular weight. Facially amphiphilic molecules with molecular weights of about 0.8 kD to about 20 kD will be more prone to leach from the surface of the substrate. The facially amphiphilic polymer may be attached or immobilized on the substrate by any appropriate method including covalent bonding, ionic interaction, coulombic interaction, hydrogen bonding or cross-linking. The polymers of the present invention provide a surface-mediated microbicide that only kills organisms in contact with the surface. Moreover the polymers of the present invention are stable and retain their bioactivity for extended periods of time and are potentially nontoxic to birds, fish, mammals and other higher organisms.

The present invention further provides a computational technique to evaluate the energy of polymer conformations and identify polymers which have the capability of exhibiting amphiphilic behavior and aid in identifying optimal sites for substitution of polar and nonpolar substituents that confer amphiphilic properties.

DETAILED DESCRIPTION OF THE INVENTION

Microbial infections represent a serious continuing problem in human and animal health. While amphiphilic α and β-peptides exhibit potent antibacterial, they are, nevertheless, difficult and expensive to prepare in large quantities. Peptides are sensitive to enzymatic and chemical hydrolysis. Exposure to microbial pathogens can occur in a variety of ways. Most objects encountered daily have the potential for harboring infectious organisms and new compounds and approaches for controlling the growth of microbes are extremely valuable and have significant commercial potential. Antimicrobial peptides related to the magainins have desirable biological activities but their utility is limited. An object the present invention is to provide new stable antimicrobial polymers which are available from inexpensive and readily available monomers and which can be incorporated into, or on to, a wide variety of materials and can withstand chemical and enzymatic degradation.

In recent years, the design of non-biological polymers with well-defined secondary and tertiary structures (S. H. Gellman et al., *Acc. Chem. Res.* 1998 31:173-80; A. E. Barron and R. N. Zuckerman, *Curr. Opin. Chem. Biol*, 1999 3:681-687; K. D. Stigers et al., *Curr. Opin. Chem. Biol,* 1999 3:714-723) has become an active area of research. One reason for this interest is that for the first time, modern methods of solid phase organic chemistry (E. Atherton and R. C. Sheppard, *Solid Phase Peptide Synthesis A Practical Approach* IRL Press Oxford 1989) have allowed the synthesis of homodisperse, sequence-specific oligomers with molecular weights approaching 5,000 Daltons. The development of this new field of homodisperse sequence-specific oligomers promises to generate molecules with novel chemical and physical properties that will span the gap between polymer and protein science. Polymers are statistical mixtures of molecules typically composed of one to a few monomers. By contrast, peptides and proteins are molecules typically composed from >15 monomers with exact control over sequence, topology, and stereochemistry. These homodisperse sequence-specific oligomers represent molecules with features of both polymers and proteins Facially amphiphilic polymers can be homopolymers wherein one monomer is substituted with both a nonpolar and a polar substituent or copolymers wherein one monomer is substituted with a polar substituent and the other monomer is substituted with a nonpolar substituent. Since the antimicrobial activity arises from the amphiphilic character conferred by a periodic pattern of side chains rather than the precise spatial arrangement of side chains, other substitution patterns are also expected to produce facially amphiphilic polymers and they all are encompassed by the present invention.

Figure 2:
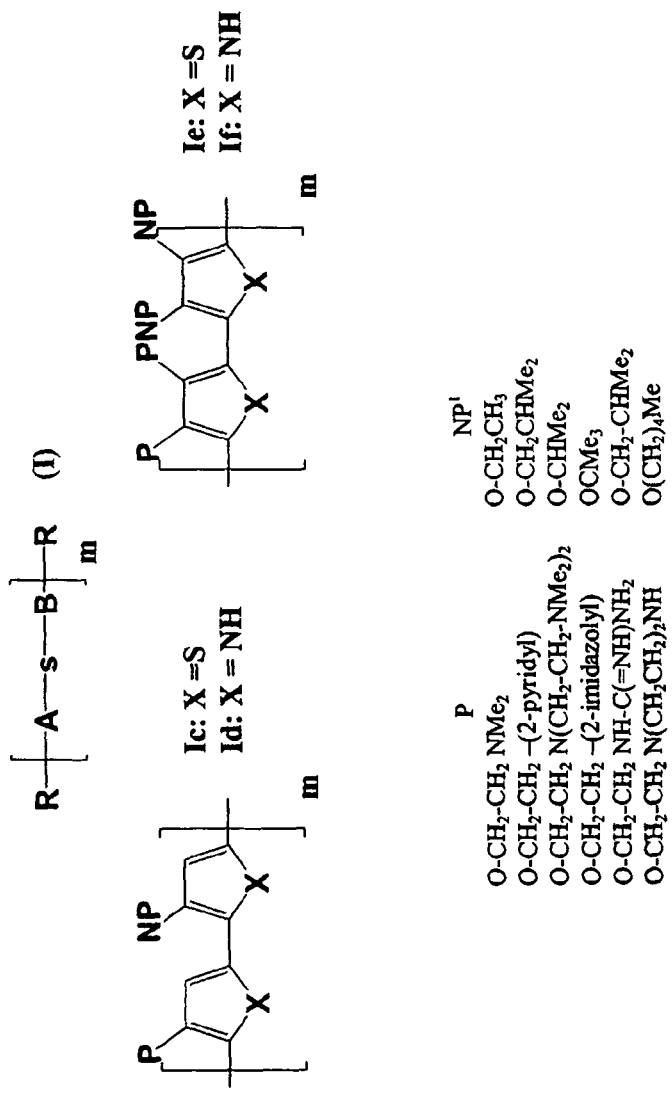
In FIG. 2 there is shown the generalized structure of arylene polymers I and typical examples of four heteroarylene monomers Ic-If.

Polyarylene and polyheteroarylene polymers represent another class of polymers which can form facially amphiphilic polymers (FIG. 1 and FIG. 2). Copolymers comprised of both aromatic and heteroaromatic monomers can also be expected to show unique properties. (U Scherf *Carbon Rich Compounds* II, 1999 20:163), Berresheim, A. J. et al., Chem. Rev. 1999 99:1747) The aromatic rings in the examples depicted in FIG. 1 have meta and para substitution pattern, one skilled in the art would immediately appreciate that equivalent polymers could be designed with an ortho orientation and these modifications can alter the conformation and the physical properties of the resulting polymer. Furthermore although the copolymers depicted in FIG. 2 have a 2,5-polyarylenes other stereochemistries are also produce facially amphiphilic heteroarylenes and the choice and the stereochemistry is often determined by the chemical reactivity of the unsubstituted monomer which determines the positions most readily functionalized. The optimal substitution patterns of polar and nonpolar substituents are determined by the conformational properties of the polymer backbone and other substitution pattern are encompassed in the invention.

The synthetic processes can be modified to produce different ranges in molecular weight and the anti-microbial polymer of the present invention will have a molecular weight selected to impart physical and chemical properties optimized for the particular application being contemplated. Traditional polymer syntheses produce a product with a range of molecular weights. The polymer chemist will readily appreciate that the chain length of these polymers can be varied by techniques know in the polymer art. Polymers of the present invention can range in molecular weight from about 800 Daltons up to about 350 kiloDaltons. Advancements in solid-phase and solution phase synthesis of amino acid oligomers have made available techniques to prepare homogeneous polymers or oligomers with defined sequence and size and these techniques can be adapted to the present invention.

The polymer design process simply requires a structure in which the repeating sequence of monomers matches the secondary structure adopted by the backbone. Once the periodicity is observed, monomers substituted with polar and nonpolar groups monomers must be prepared and introduced to produce a cationic, amphiphilic secondary. As exemplified in FIGS. 1 and 2 these arylene polymers can be homopolymers (FIG. 1 Ia) or copolymers (FIG. 1 Ib and FIG. 2 Ic-f). The monomers are not limited to monocyclic aryl compounds and polycyclic aromatics (If) can be advantageously employed to modify the distances between groups which will alter the periodicity of the subunits.

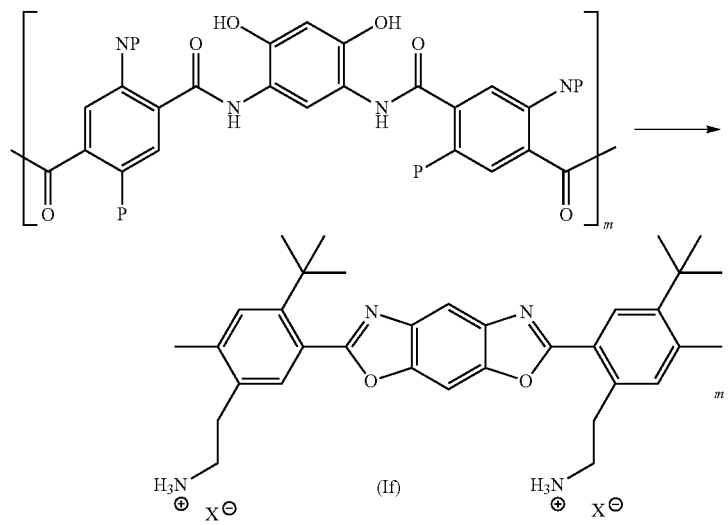

Additional molecular features can be added to the macromolecular backbone to promote the desired secondary structure and disfavor other structures thereby combining elements of both positive and negative design. Conformational studies on biofoldamers (proteins and RNA), and early work with a variety of sequence-specific polymers, have shown that several elements are crucial in order for the polymers to adopt the desired folded conformation. Key elements include strong electrostatic interactions (i.e., intramolecular hydrogen bonding) between adjacent or more distant monomers, rigidification caused by the backbone torsions or by bulky functional groups, and π-π stacking interactions between noncontiguous aromatic units.

Magainin and the other naturally occurring antibacterial peptides exhibit considerable variation in their chain length, hydrophobicity and distribution of charges. These linear peptides do, however, contain positively charges amino acids and a large hydrophobic moment resulting in a high propensity to adopt α-helical conformations in a hydrophobic environment, e.g., a cell surface or a natural or synthetic membrane. (Z. Oren and Y. Shai Biopolymers (Peptide Science), 1998 47:451-463.) The periodic distribution of hydrophobic and hydrophilic side chains in their amino acid sequences allows the segregation of the hydrophobic and hydrophilic side chains to opposite faces of the cylinder formed by the helix. The overall amphiphilicity, not the specific sequence, secondary structure or chirality, correlates best with anti-microbial activity. Thus it appears that any suitably amphiphilic material (not necessarily an α-helix or β-sheet) would have antimicrobial properties. The necessary condition for forming a facially amphiphilic structure is the molecule should have a repeating pattern of polar and nonpolar side chains whose periodicity is approximately the same as that of the secondary structure of interest.

The term "microorganism" as used herein includes bacteria, algae, fungi, yeast, mycoplasmids, parasites and protozoa.

The term "antimicrobial", "microbiocidal" or "biocidal" as used herein means that the materials inhibit, prevent, or destroy the growth or proliferation of microorganisms. This activity can be either bacteriocidal or bacteriostatic. The term "bacteriocidal" as used herein means the killing of microorganisms. The term "bacteriostatic" as used herein means inhibiting the growth of microorganisms which can be reversible under certain conditions.

The term "polymer" as used herein refers to a macromolecule comprising a plurality of repeating units or monomers. The term includes homopolymers, which are formed from a single type of monomers and copolymers that are formed from two or more different monomers. In copolymers the monomers may be distributed randomly (random copolymer), in alternating fashion (alternating copolymer) or in blocks (block copolymer). The polymers of the present invention are either homopolymers or alternating copolymers. The term "polymer" as used herein is intended to exclude proteins, peptides, polypeptides and other proteinaceous materials composed exclusively of α or β-amino acids. The term "oligomer" as used herein refers to a homogenous polymer with a defined sequence and molecular weight.

The term "polymer backbone" or "backbone" as used herein refers to that portion of the polymer which is a continuous chain comprising the bonds formed between monomers upon polymerization. The composition of the polymer backbone can be described in terms of the identity of the monomers from which it is formed without regard to the composition of branches, or side chains, off the polymer backbone.

The term "polymer side chain" or "side chain" refers to portions of the monomer which, following polymerization, forms an extension off the polymer backbone. In homopolymers all the polymer side chains are derived from the same monomer. A copolymer can comprise two or more distinct side chains from different monomers.

The term "alkyl" as used herein denotes a univalent saturated branched or straight hydrocarbon chain. Unless otherwise stated such chains contain from 1 to 18 carbon atoms.

Representative of such alkyl groups are methyl, ethyl, propyl, iso-propyl, sec-butyl, tert-butyl, pentyl, neo-pentyl, iso-pentyl, hexyl, iso-hexyl, heptyl, octyl, nonyl, decyl, tridecyl, tetradecyl, hexadecyl octadecyl, and the like. When qualified by "lower" the alkyl group will contain from 1 to 6 carbon atoms. The term "cycloalkyl" as used herein denotes a univalent cyclic hydrocarbon chain. Representative groups are cyclopropyl, cyclobutyl, cyclohexyl, cyclopentyl and cyclohexyl.

The phrase "groups with chemically nonequivalent termini" refers to functional groups such as esters amides, sulfonamides and N-hydroxyoximes where reversing the orientation of the substituents, e.g. $R^1C(=O)OR^2$ vs. $R^1O(O=)CR^2$, produces unique chemical entities.

The term "basic heterocycle" as used herein denotes cyclic atomic array which includes a nitrogen atom that has a pKa greater than about 5 and that is protonated under physiological conditions. Representative of such basic heterocycles are pyridine, quinoline, imidazole, imidazoline, cyclic guanidines, pyrazole, pyrazoline, dihydropyrazoline, pyrrolidine, piperidine, piperazine, 4-alkylpiperazine, and derivatives thereof such as 2-aminopyridine, 4-aminopyridine, 2-aminoimidazoline, 4-aminoimidazoline or VII where $X^1$ is O, N, S or absent and i is 2 to 4.

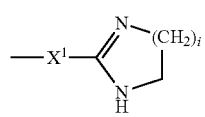

(VII)

The term "amphiphilic" as used herein describes a three-dimensional structure having discrete hydrophobic and hydrophilic regions. An amphiphilic polymer requires the presence of both hydrophobic and hydrophilic elements along the polymer backbone. The presence of hydrophobic and hydrophilic groups is a necessary, but not sufficient, condition to produce an amphiphilic molecule or polymer. Polymers frequently adopt a random or disordered conformation in which the side chains are located randomly in space and there are no distinctive hydrophobic and hydrophilic regions.

The term "facially amphiphilic" or "facial amphiphilicity" as used herein describes polymers with polar (hydrophilic) and nonpolar (hydrophobic) side chains that adopt conformation(s) leading to segregation of polar and nonpolar side chains to opposite faces or separate regions of the structure. This structure can comprise any of the energetically accessible low-energy conformations for a given polymer backbone. Additionally random or block copolymers may adopt random backbone conformations that do not lead to distinct hydrophilic and hydrophobic regions or which do not segregate along different faces of the polymer. These copolymers are not facially amphiphilic as defined herein.

The term "naturally occurring amino acids" means the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, carboxyglutamic acid, arginine, omithine and lysine. Unless specifically indicated, all amino acids referred to in this application are in the L-form.

The term "side chain of a naturally occurring amino acid" as used herein refers to the substituent on the α-carbon of an α amino acid. The tem "polar side chain of a naturally occurring amino acid" refers to the side chain of a positively charged, negatively charged or hydrophilic amino acid. The tem "nonpolar side chain of a naturally occurring amino acid" refers to the side chain of a hydrophobic amino acid.

The term "positively charged amino acid" or "cationic amino acid" as used herein includes any naturally occurring or unnatural amino acid having a positively charged side chain under normal physiological conditions. Examples of positively charged naturally occurring amino acids are arginine, lysine and histidine.

The term "negatively charged amino acid" includes any naturally occurring or unnatural amino acid having a negatively charged side chain under normal physiological conditions. Examples of negatively charged naturally occurring amino acids are aspartic acid and glutamic acid.

The term "hydrophilic amino acid" means any amino acid having an uncharged, polar side chain that is relatively soluble in water. Examples of naturally occurring hydrophilic amino acids are serine, threonine, tyrosine, asparagine, glutamine, and cysteine.

The term "hydrophobic amino acid" means any amino acid having an uncharged, nonpolar side chain that is relatively insoluble in water. Examples of naturally occurring hydrophobic amino acids are alanine, leucine, isoleucine, valine, proline, phenylalanine, tryptophan and methionine.

An embodiment of the present invention is a facially amphiphilic polymer of formula I

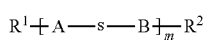

(I)

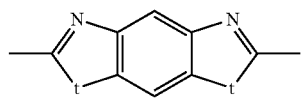

(VI)

wherein:
A and B are independently optionally substituted o-, m-, p-phenylene or optionally substituted heteroarylene wherein either (i) A and B are both substituted with a polar (P) group and a nonpolar (NP) group, (ii) one of A or B is substituted with a polar (P) group and a nonpolar (NP) group and the other of A or B is substituted with neither a polar (P) group nor a nonpolar (NP) group, or (iii) one of A or B is substituted with one or two polar (P) group(s) and the other of A or B is substituted with one or two nonpolar (NP) group(s), or (iv) one of A or B is substituted at the 2 position with a polar (P) group and at the 5- or 6-position with a nonpolar (NP) group and the other of A or B is substituted with a non-polar group; or,
A is as defined above and substituted with a polar (P) group and a nonpolar (NP) group, and B is a group C≡C $(CH_2)_p$ C≡C wherein p is as defined below;
s is absent, or represents a single, double or triple bond, or VI optionally substituted with polar (P) and nonpolar (NP) groups wherein t is O or S;
$R^1$ is (i) halo and $R^2$ is hydrogen; or (ii) C-s-B-s- and $R^2$ is C; or, (iii) C-s- and $R^2$ is -A-s-C wherein C is pyridine or phenyl said pyridine or phenyl optionally substituted with 1 or 2 substituents independently selected from a group consisting of halo, nitro, cyano, $C_1$-$C_6$ alkoxy, $C_1$-$C_6$ alkoxycarbonyl, and benzyloxycarbonyl; or, $R^1$ and $R^2$ together are s;

NP is a nonpolar group an independently selected from $R^4$ or —U—$(CH_2)_p$—$R^4$ wherein $R^4$ is selected from a group consisting of hydrogen, $C_1$-$C_{10}$ alkyl, $C_3$-$C_{18}$ branched alkyl, $C_3$-$C_8$ cycloalkyl, monocyclic or polycyclic phenyl optionally substituted with one or more $C_1$-$C_4$ alkyl or halo groups and monocyclic or polycyclic heteroaryl optionally substituted with one or more $C_1$-$C_4$ alkyl or halo groups and U and p are as defined below;

P is a polar group selected from a group consisting of III, hydroxyethoxymethyl, methoxyethoxymethyl and polyoxyethylene

(III)

wherein;

U is absent or selected from a group consisting of O, S, S(=O), S(=O)$_2$, NH, —C(=O)O—, —C(=O)NH—, —C(=O)S—, —C(=S)NH—, —S(=O)$_2$NH—, and C(=NO—) wherein groups with two chemically non-equivalent termini can adopt both possible orientations;

V is selected from a group consisting of amino, hydroxyl, $C_1$-$C_6$ alkylamino, $C_1$-$C_6$ dialkylamino, NH(CH$_2$)$_p$NH$_2$, N(CH$_2$CH$_2$NH$_2$)$_2$, amidine, guanidine, semicarbazone, basic heterocycle, and phenyl optionally substituted with an amino, $C_1$-$C_6$ alkylamino, $C_1$-$C_6$ dialkylamino and lower acylamino optionally substituted with one or more amino, lower alkylamino or lower dialkylamino;

and the alkylene chain is optionally substituted with an amino or hydroxyl group or unsaturated;

p is independently 0 to 8; and, m is 2 to at least about 500.

with the proviso that if A and B are thiophene the polar groups cannot be 3-(propionic acid) or methoxy(diethoxy)ethyl and the nonpolar group cannot be n-dodecyl.

Yet another embodiment of the present invention is a facially amphiphilic polymer of formula I wherein:

A and B are independently optionally substituted o-, m-, or p-phenylene;

s is absent or represents a single, double or a triple bond;

NP is a nonpolar group independently selected from $R^4$ or —U—$(CH_2)_p$—$R^4$ wherein $R^4$ is selected from a group consisting of hydrogen, $C_1$-$C_4$ alkyl, $C_3$-$C_{12}$ branched alkyl, $C_3$-$C_8$ cycloalkyl, phenyl optionally substituted with one or more $C_1$-$C_4$ alkyl groups and heteroaryl optionally substituted with one or more $C_1$-$C_4$ alkyl groups and U and p are as defined below;

P is a polar group selected from a group consisting of III, hydroxyethoxymethyl, methoxyethoxymethyl or polyoxyethylene

(III)

wherein:

U is absent, O, S, SO, SO$_2$, or NH;

V is selected from a group consisting of amino, hydroxyl, $C_1$-$C_6$ alkylamino, $C_1$-$C_6$ dialkylamino, NH(CH$_2$)$_p$NH$_2$, N(CH$_2$CH$_2$NH$_2$)$_2$, amidine, guanidine, semicarbazone, imidazole, piperidine, piperazine, 4-alkylpiperazine and phenyl optionally substituted with an amino, $C_1$-$C_6$ alkylamino, $C_1$-$C_6$ dialkylamino and lower acylamino optionally substituted with one or more amino, lower alkylamino or lower dialkylamino;

the alkylene chain is optionally substituted with an amino or hydroxyl group or unsaturated;

p is independently 0 to 8; and, m is 2 to at least about 500.

Still another embodiment of the present invention is a facially amphiphilic polymer of formula I wherein:

A and B are independently optionally substituted m-phenylene wherein (i) A is substituted at the 5-position with a nonpolar (NP) group and B is substituted at the 5-position with a nonpolar (P) group, (ii) A is substituted at the 2-position with a polar (P) and at the 5-position with a nonpolar (NP) group and B is substituted at the 2-position with a nonpolar (NP) group and at the 5-position with a polar (P) group, (iii) one of A or B is substituted at the 2-position with a polar group and the 5-position with a nonpolar group and the other of A or B is substituted by neither a polar group nor a nonpolar group; or, (iv) one of A or B is substituted at the 5-position with a polar group and the 2-position with a nonpolar group and the other of A or B is substituted by neither a polar group nor a nonpolar group;

s is absent or represents a single, double or a triple bond;

NP is a nonpolar group independently selected from $R^4$ or —U—$(CH_2)_p$—$R^4$ wherein $R^4$ is selected from a group consisting of hydrogen, methyl, ethyl, n-propyl, iso-propyl, n-butyl, iso-butyl, sec-butyl, tert-butyl, n-pentyl, iso-pentyl, and sec-pentyl and U and p are as defined below;

P is a polar group U—$(CH_2)_p$—V wherein U is absent or selected from a group consisting of O and S, and V is selected from a group consisting of amino, lower alkyl amino, lower dialkylamino, imidazole, guanidine, NH(CH$_2$)$_p$NH$_2$, N(CH$_2$CH$_2$NH$_2$)$_2$, piperidine, piperazine, 4-alkylpiperazine;

p is independently 0 to 8; and m is 2 to at least about 500.

Another embodiment of the present invention is a facially amphiphilic polymer according of formula XIX

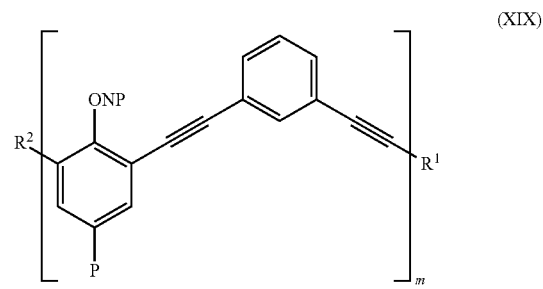

(XIX)

wherein

NP is methyl, ethyl, n-propyl, iso-propyl, n-butyl, iso-butyl, n-butyl, sec-butyl, tert-butyl, n-pentyl, iso-pentyl, and sec-pentyl;

P is a polar group U—$(CH_2)_p$—V wherein U is O or S, p is 0 to 8 and V is selected from a group consisting of amino, lower alkyl amino, lower dialkylamino, guanidine, pyridine, piperazine, 4-alkylpiperazine;

p is 0 to 8; and, m is 2 to at least about 30.

Still another embodiment of the present invention is a facially amphiphilic polymer of formula XX

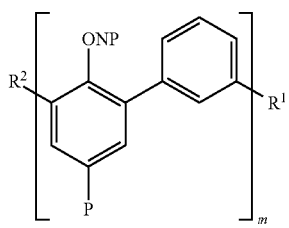
(XX)

wherein

NP is methyl, ethyl, n-propyl, iso-propyl, n-butyl, iso-butyl, n-butyl, sec-butyl, tert-butyl, n-pentyl, iso-pentyl, and sec-pentyl;

P is a polar group U—$(CH_2)_p$—V wherein U is O or S, p is 0 to 8 and V is selected from a group consisting of amino, lower alkyl amino, lower dialkylamino, guanidine, pyridine, piperazine, 4-alkylpiperazine;

p is 0 to 8; and, m is 2 to at least about 30.

Another embodiment of the present invention is a polymer according to claim 1 comprising a compound of formula I wherein:

A and B are independently optionally substituted p-phenylene wherein (i) A is substituted at the 2-position with a nonpolar (NP) group and B is substituted at the 5- or 6-position with a nonpolar (P) group, (ii) both A and B are substituted with a polar (P) group at the 2-position and a nonpolar (NP) group at the 5- or 6-position; or, (iii) one of A or B is substituted at the 2 position with a polar (P) group and at the 5- or 6-position with a nonpolar (NP) group and the other of A or B is substituted with neither a polar group nor a non-polar group;

s is absent or represents a single, double or a triple bond;

NP is a nonpolar group independently selected from $R^4$ or —U—$(CH_2)_p$—$R^4$ wherein $R^4$ is selected from a group consisting of hydrogen, methyl, ethyl, n-propyl, iso-propyl, n-butyl, iso-butyl, sec-butyl, tert-butyl, n-pentyl iso-pentyl, and sec-pentyl and U and p are as defined below;

P is a polar group U—$(CH_2)_p$—V wherein U is absent or selected from a group consisting of O and S, and V is selected from a group consisting of amino, lower alkyl amino, lower dialkylamino, imidazole, guanidine, $NH(CH_2)_pNH_2$, $N(CH_2CH_2NH_2)_2$, piperidine, piperazine, 4-alkylpiperazine;

p is independently 0 to 8; and, m is 2 to at least about 500.

Another embodiment of the present invention is a facially amphiphilic polymer according of formula I wherein:

A and B are independently optionally substituted p-phenylene wherein (i) A is substituted at the 2-position with a nonpolar (NP) group and B is substituted at the 5- or 6-position with a nonpolar (P) group, (ii) both A and B are substituted with a polar (P) group at the 2-position and a nonpolar (NP) group at the 5- or 6-position; or, (iii) one of A or B is substituted at the 2 position with a polar (P) group and at the 5- or 6-position with a nonpolar (NP) group and the other of A or B is substituted with neither a polar group nor a non-polar group;

s is absent or represents a single, double or a triple bond;

NP is a nonpolar group independently selected from $R^4$ or —U—$(CH_2)_p$—$R^4$ wherein $R^4$ is selected from a group consisting of hydrogen, methyl, ethyl, n-propyl, iso-propyl, n-butyl, iso-butyl, sec-butyl, tert-butyl, n-pentyl iso-pentyl, and sec-pentyl and U and p are as defined below;

P is a polar group U—$(CH_2)_p$—V wherein U is absent or selected from a group consisting of O and S, and V is selected from a group consisting of amino, lower alkyl amino, lower dialkylamino, imidazole, guanidine, $NH(CH_2)_pNH_2$, $N(CH_2CH_2NH_2)_2$, piperidine, piperazine, 4-alkylpiperazine;

p is independently 0 to 8; and, m is 2 to at least about 500.

Yet another embodiment of the present invention is a facially amphiphilic polymer of compound I wherein:

A and B are independently optionally substituted heteroarylene wherein one of A or B is substituted with one or two polar (P) group(s) and the other of A or B is substituted with one or two nonpolar (NP) group(s);

s is absent or represents a single, double or a triple bond;

NP is a nonpolar group independently selected from $R^4$ or —U—$(CH_2)_p$—$R^4$ wherein $R^4$ is selected from a group consisting of hydrogen, $C_1$-$C_4$ alkyl, $C_3$-$C_2$ branched alkyl, $C_3$-$C_8$ cycloalkyl, and heteroaryl optionally substituted with one or more $C_1$-$C_4$ alkyl groups and U and p are as defined below;

P is a polar group selected from a group consisting of III, hydroxyethoxymethyl, methoxyethoxymethyl or polyoxyethylene,

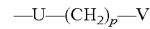
(III)

wherein,

U is absent, O, S, SO, $SO_2$, or NH;

V is selected from a group consisting of amino, hydroxyl, $C_1$-$C_6$ alkylamino, $C_1$-$C_6$ dialkylamino, $NH(CH_2)_p NH_2$, $N(CH_2CH_2NH_2)_2$, amidine, guanidine, semicarbazone, imidazole, piperidine, piperazine, 4-alkylpiperazine and phenyl optionally substituted with an amino, $C_1$-$C_6$ alkylamino, $C_1$-$C_6$ dialkylamino and lower acylamino optionally substituted with one or more amino, lower alkylamino or lower dialkylamino; and, the alkylene chain is optionally substituted with an amino or hydroxyl group or unsaturated;

p is independently 0 to 8; and, m is 2 to at least about 500.

Still another embodiment of the present invention is a facially amphiphilic polymer of formula I wherein:

A and B are independently optionally substituted 2,5-thiophenylene or 2,5-pyrrolene wherein (i) A is substituted at the 3-position with a nonpolar (NP) group and B is substituted at the 3-position with a polar (P), (ii) A is substituted at the 3-position with a nonpolar (NP) group and B is substituted at the 4-position with a polar (P) group, or (iii) one of A or B is substituted at the 3 and 4-position with a nonpolar (NP) group and the other of A or B is substituted at the 3 and 4-position with a polar (P) group;

s is absent or represents a single, double or a triple bond;

NP is a nonpolar group independently selected from $R^4$ or —U—$(CH_2)_p$—$R^4$ wherein $R^4$ is selected from a group consisting of hydrogen, methyl, ethyl, n-propyl, iso-propyl, iso-butyl, sec-butyl, tert-butyl, iso-pentyl, and sec-pentyl and U and p are as defined below;

P is a polar group U—(CH$_2$)$_p$—V wherein U is absent or selected from a group consisting of O and S, and V is selected from a group consisting of amino, lower alkyl amino, lower dialkylamino, imidazole, guanidine, NH(CH$_2$)$_p$NH$_2$, N(CH$_2$CH$_2$NH$_2$)$_2$, piperidine, piperazine, 4-alkylpiperazine;

p is independently 0 to 8; and;

m is 2 to at least about 500.

Polyphenylene and polyheteroarylene polymers can be prepared regiospecifically by utilizing palladium(0) coupling reactions as developed by Hecht, Stille, Suzuki and others. Bjornholm et al. utilized a series of Pd(0) mediated organotin coupling reactions to prepare polythiophenes and similar chemistry can be adapted to any aromatic polymer. McCullough and Loewe have described the preparation of poly-(3-substituted)thiophenes by Ni(II) catalyzed coupling of organomagnesium derivatives (R. D. McCullough and R. S. Lowe, U.S. Pat. No. 6,166,172) and Camps et al. have described related methodology for the synthesis of heterocyclic/aromatic electric-conducting copolymers (M. Camps et al. U.S. Pat. No. 4,508,639). Alternatively, heterocyclic polymers can be prepared by electrolysis. Aromatic and heteroaromatic monomers in the present invention can also be linked by polybenzoazoles (If) and polybenzothiazoles. These compounds can be prepared by coupling a suitable substituted terephthalic derivative with either 1,3-diamino-4,6-dihydroxybenzene or 1,3-diamino-4,6-dimercaptobenzene in the presence of dehydrating agents (M. P. Stevens, *Polymer Chemistry*, Oxford University Press, 1999, p. 417).

Figure 3:
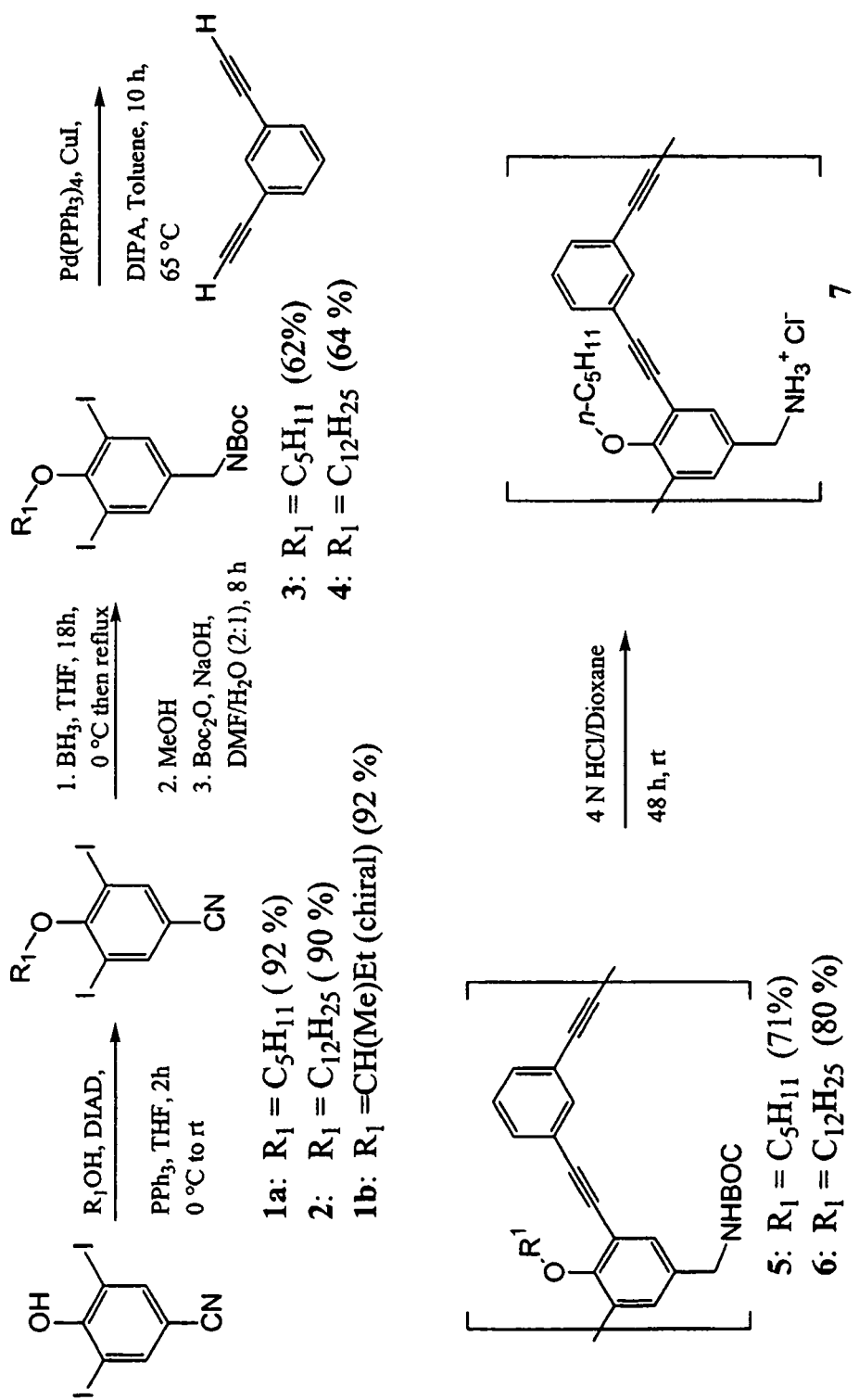
In FIG. 3 there is shown the synthesis of a phenylene ethynylene oligomer.

The syntheses of appropriately substituted monomers are straightforward. The preparation of monomers for meta-phenylene derivatives is depicted in FIG. 3. Ortho and para dihalides or boronic acids are suitable precursors for a variety of coupling reactions and numerous pathways are available to incorporate of polar and nonpolar side chains. Phenolic groups on the monomer can be alkylated to produce polar and nonpolar substituents. Alkylation of the commercially available phenol will be accomplished with standard Williamson ether synthesis for the non-polar side chain with ethyl bromide as the alkylating agent. Polar sidechains can be introduced with bifunctional alkylating agents such as BOC-NH(CH$_2$)$_2$Br. Alternatively the phenol group can be alkylated to install the desired polar side chain function by employing Mitsonobu reaction with BOC-NH(CH$_2$)$_2$—OH, triphenyl phosphine, and diethyl acetylenedicarboxylate, The processes required for the synthesis of appropriate monomers is well known in the art.

Antimicrobial testing is carried out using the micro-broth dilution technique with *E. coli*. Other organisms screened include ampicillin and streptomycin-resistant *E. coli* D31, *B. subtilis*, vancomycin-resistant *Enterococcus faecium* A436, and methicillin-resistant *S. aureus* 5332. Any peptide that is found to be active will be purified to homogeneity, and retested to obtain an accurate IC$_{50}$. Secondary screens include *Klebsiella pneumoniae* Kp1, and *Salmonella typhimunium* S5, and *Pseudomonus aeruginosa* 10. Traditionally, the micro-broth dilution technique only evaluates a single data point between 18-24 hours; however, the measurements can be extended to 24 hr to monitor cell growth through the entire growth phase. These experiments are performed in LB medium (which is a rich medium typically used to grow cells for protein expression) and represent a critical initial screen for activity. Since salt concentrations, proteins, and other solutes can affect the activities of antibiotics, materials that showed no activity in rich medium were retested in minimal medium (M9) to determine if rich medium was limiting activity. No relationship between the media and the activity was observed which is consistent with the mode of action is believed to be through general membrane disruption To determine the toxicity to mammalian, as well to bacterial, cells the biocidal activity is evaluated using both cultured cells and freshly obtained human blood cells. Increasing concentration of polymer will be added to both confluent and non-confluent cultures of human umbilical endothelial cells (HUVEC, Cambrex). Cell number, monolayer integrity, and cell viability (measured as trypan blue exclusion) will be evaluated as a function of time in culture.

While the synthesis of a variety of polymer backbones is well understood, computer-aided computational techniques can provide valuable insight and guidance in the selection of potential antimicrobial polymers. The goal of these computations is to identify potential low energy conformations which have a geometrical repeat that matches a convenient sequence repeat of less than 6 monomer units. For example in α-amino acid oligomers, the geometrical repeat of the β-sheet is 2.0 residues. Once these repeating scaffolds are identified and the frequency of the repeat is calculated, polar and nonpolar substituents can be incorporated into the monomers to confer amphiphilic properties into the molecule.

High level ab initio calculations are one technique which will identify accessible low energy conformations. Unfortunately, these techniques, while extremely powerful, are not practical with molecules the size of the present invention. Molecular Dynamics simulations provide an alternative that can be adapted efficiently to molecules envisioned in the present invention. Key elements in determining conformational energies are strong electrostatic interactions (i.e., intramolecular hydrogen bonding) between adjacent or more distant monomers and rigidification caused by the backbone torsions or by bulky fuinctional groups. In order to simulate these interactions in molecular mechanics calculations the empirical parameters, i.e., a force field, must be determined for representative polymer backbones. Density functional theory (DFT) can be used to carry out ab initio calculations on small model compounds that share the basic structural connectivity of the polymer backbones and which will generate required torsional potentials. The procedure to carry out these computations is:

1. Select simple model compounds that share similar torsional patterns with the target polymer backbones.
2. For each compound, perform a full geometric optimization at the BLYP/6-31G(d) level of theory (multiple initial configurations ensure the global minimum is obtained).
3. Calculate the single-point energy at the most stable geometry obtained in step 2 above, using B3LYP/6-311 G++(dp) or plane wave CPMD.
4. Constrain a relevant torsion to a set angle and repeat steps 2 and 3.
5. Repeat step 4 for several angles; the torsional energy is obtained by subtracting the non-bonded interactions.
6. Fit energies versus torsion angle to a cosine series whose coefficients are the force field parameters.

After verifying the suitability of the force field by comparing computed predictions of the structure and thermodynamic properties to molecules that have similar torsional patterns and for which experimental data are available, the fitted torsions are then combined with bond stretching, bending, one-four, vander Waals, and electrostatic potentials borrowed from the CHARMM (B. R. Brooks et al. *J. Comp. Chem.* 1983 4:187-217 and TraPPE (M. G. Martin and J. I. Siepmann, *J. Phys. Chem B*. 0.1999103:4508-17; C. D. Wick et al. *J. Phys. Chem B*. 0.2000 104:3093-3104) molecular dynamics force fields. To identify conformations that can adopt periodic folding patterns with polar groups and apolar groups lined up on the opposite sides. Initial structures can be obtained with the Gaussian package (M. Frisch et aL Gaussian 98 (revision A.7) Gaussian Inc., Pittsburgh, Pa. 1998). Then, the parallelized plane-wave Car-Parrinello CP-MD (R, Car and M. Parrinello *Phys. Rev. Lett.* 1985 55:2471-2474) program, (cf U. Röthlisberger et al. *J. Chem. Phys.* 1996 3692-3700) is used to obtain energies at the minimum and constrained geometries. The conformations of the polymers without side-chains can be investigated in the gas phase. Both MD and MC methods will be used to sample the conformations. The former is useful for global motions of the polymer. With biasing techniques (J. I. Siepmann and D. Frenkel *Mol. Phys.* 1992 75:59-70; M. G. Martin and J. I. Siepmann *J. Phys. Chem. B* 1999 103:4508-4517; T. J. H. Vlugt et al. *Mol. Phys.* 1998 94:727-733) the latter allows efficient sampling for polymers with multiple local minimum configurations that are separated by relatively large barriers.

The potential conformations are examined for positions to attach pendant groups that will impart amphiphilic character to the secondary structure. Polymers selected from the gas-phase studies with suitable backbone conformations and with side-chains at the optimal positions to introduce amphiphilicity will be further evaluated in a model interfacial system, n-hexane/water, chosen because it is simple and cheap for calculations while it mimics well the lipid/water bilayer environment. Polymer secondary structures that require inter-polymer interactions can be identified by repeating the above-mentioned calculations using a periodically repeated series of unit cells of various symmetries (so called variable cell molecular dynamics or Monte Carlo technique) with or without solvent. The results of these calculations will guide the selection of candidates for synthesis.

An embodiment of the present is a computation technique to identify polymer backbones which can produce facially amphiphilic polymers by:
(1) selecting a polymer backbones or scaffolds suitable for regiospecific introduction of polar (P) and nonpolar (NP) groups;
(2) determining parameters for a molecular mechanics force field utilizing ab initio quantum mechanical calculations;
(3) calculating energetically accessible conformations of said backbone using molecular dynamics or molecular mechanics calculations;
(4) identifying energetically accessible conformations of said backbone wherein the periodicity of a geometrical/conformational repeat matches a sequence repeat;
(5) synthesizing monomers with polar and nonpolar substituents;
(6) synthesizing an antimicrobial polymer containing said monomers by solution or solid-phase synthesis.

The facially amphiphilic polymers of the present invention can have a substantial range in molecular weight. Facially amphiphilic molecules with molecular weights of about 0.8 kD to about 20 kD will be more prone to leach from the surface of the substrate. The facially amphiphilic polymer may be attached to, applied on or incorporated into almost any substrate including but not limited to woods, paper, synthetic polymers (plastics), natural and synthetic fibers, natural and synthetic rubbers, cloth, glasses and ceramics by appropriate methods including covalent bonding, ionic interaction, coulombic interaction, hydrogen bonding or cross-linking. Examples of synthetic polymers include elastically deformable polymers which may be thermosetting or thermoplastic including, but not limited to polypropylene, polyethylene, polyvinyl chloride, polyethylene terephthalate, polyurethane, polyesters, such as polylactide, polyglycolide, rubbers such as polyisoprene, polybutadiene or latex, polytetrafluoroethylene, polysulfone and polyethylenesulfone polymers or copolymers. Examples of natural fibers include cotton, wool and linen.

The polymers of the present invention thus provide a surface-mediated microbicide that only kills organisms in contact with the surface. Moreover the polymers of the present invention are stable and retain their bioactivity for extended periods of time. Polymers bound to the surface will not leach out of the surface into the environment. Specificity can be imparted for microbial cell walls which can provide polymers with reduced toxicity to birds, fish, mammals and other higher organisms.

Any object that is exposed to or susceptible to bacterial or microbial contamination can be treated with these polymers. These needs are particularly acute in the health care and food industries. A growing concern with preservatives has produced a need for new materials that prevent microbiological contamination without including preservatives. The incidence of infection from food-borne pathogens is a continuing concern and antimicrobial packaging material, utensils and surfaces would be valuable. In the health care and medical device areas the utility of antimicrobial instruments, packaging and surfaces are obvious. Products used internally or externally in humans or animal health including, but not limited to, surgical gloves, implanted devices, sutures, catheters, dialysis membranes, water filters and implements, all can harbor and transmit pathogens. The polymers of the present invention can be incorporated into spinnable fibers for use in materials susceptible to bacterial contamination including fabrics, surgical gowns, and carpets. Ophthalmic solutions and contact lenses easily become contaminated and cause ocular infections. Antimicrobial storage containers for contact lens and cleaning solutions would be very valuable. Both pets and agronomic animals are exposed to and harbor a variety of infectious pathogenic organisms that can cause disease in animals or humans. Coatings, paints adhesives all are exposed to microbial contamination by and are used in locations where microbial growth is undesirable.

Traditionally, monolayers have been created at air/water interfaces and transferred to a variety of surfaces for chemical and structural characterization, as documented in a large body of work dating back to the seminal studies of Blodgett and Langmuir. Monolayers can be chemically bonded to solid supports, resulting in stable, uniformly packed molecular layers that self-assemble by absorption. Typically, these Self-Assembled Monolayers (SAMS) are covalently tethered to solids using either alkylsiloxane or thiolate-gold linkages. Alkylthiolate-gold linkages can be formed on the surface of gold by spontaneous absorption of a thiol or disulfide. Gold layers can be deposited on most solid surfaces, providing great versatility. Alkylsiloxane monolayers can be prepared by reacting trialkoxysilanes or trichlorosilanes with a silicon dioxide surface resulting in a monolayer of crosslinked siloxanes on the surface. Siloxane monolayers may be frowned on any solid that contains surface silanol groups including atomically smooth, surface-oxidized silicon wafers, glass and quartz. These two chemistries will allow amphiphilic polymers to be attached a variety of surfaces.

These amphiphilic polymers can incorporate linkers to allow the polymers to more efficiently interact with the environment around the solid surface. Tethering chemistries that allow presentation of peptides and proteins in native conformations with minimal interaction with the underlying substrate have been described. For examples, alkanethiols of the general form, $HS-(CH_2)_{11}-(OCH_2-CH_2)_n-OH$ (denoted HS—$C_{11}$-En, n=3-6), have now come into widespread use for studies of receptor/ligand interactions (M. Mrksich *Cell Mol. Life Sci.* 1998 54:653-62; M. Mrksich and G. M. Whitesides *Ann. Rev. Biophys. Biomol. Struct.* 1996 25:55-78). Polyethylene glycol derived amino acids, e.g. Fmoc-NH—($CH_2$—$CH_2$—O)$_2$)$CH_2$—COOH (Neosystems) have also been described Cys will be appended to the N-terminus to act as a group that allows coupling via its thiol, directly or through chemoselective ligation (T. W. Muir et al. *Methods Enzymol.* 1997 289:266-98; G. G. Kochendoerfer et aL *Biochemistry* 1999 38:11905-13). The thiol group serves to tether the molecule to gold surfaces, while the terminal hydroxyl and ethylene glycol groups project towards solvent, presenting a hydrophilic surface. Attachment to siloxane and polyethylene surfaces have also been described. (S. P. Massia and J. Stark *J. Biomed. Mat. res.* 200156:390-9; S. P. Massia and J. A. Hubbell *J. Cell Biol.* 1991114:1089-1100; S. P. Massia and J. A. Hubbell *Anal. Biochem.* 1990 187:292-301; B. T. Houseman and M. Mrksich *Biomaterials* 200122:943-55).

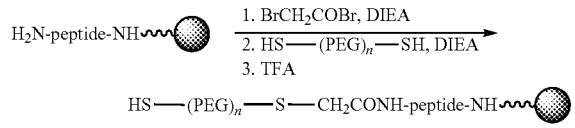

Resin bound intermediates can easily be modified to incorporate linkers. Glass surfaces can be modified to allow reaction with the thiol groups of the peptide by: (i) aminoalkylation of the glass surface by treatment with trimethoxysilylpropylamine; (ii) reaction of the amino groups with a bromoacetyl bromide or other heterobifluctional crosslinker groups capable of also reacting with a thiol group. In the above example, we show an amino surface in which we have introduced bromoacetyl groups for subsequent reaction with peptide thiols. Alternatively, thiol-reactive maleimides, vinyl-sulfones (Michael acceptors) may be incorporated using commercially available cross-linking agents. Alternatively, the surface amino groups may be converted to carboxylates by treatment with an anhydride, and then converted to thioesters under standard conditions. The resulting thioesters react facilely and with extreme regioselectivity with an N-terminal Cys residue. By incorporating quantities of inactive "filler" molecule, e.g. one example which is not limiting is a monofimctional thiol-terminated short chain polyethylene glycol polymer with the reactive teathering group the molar ratio of the oligomer to the "filler" component, it should be possible to continuously vary the surface density of the polymers attached to a solid support.

An embodiment of the present invention is a process for producing an antimicrobial surface by attaching a antimicrobial facially amphiphilic polymer to a surface comprising treating said surface with a first chemically reactive group and reacting a facially amphiphilic polymer linked to a second reactive group thereto.

Another embodiment of the present invention is a process for attaching a facially amphiphilic polymer to a surface wherein the solid surface is treated with a 1-(trialkoxysilyl) alkylamine and facially amphiphilic polymer contains an activated carboxylic acid.

Yet another embodiment of the present invention is a process for attaching a facially amphiphilic polymer to a surface wherein the solid surface is treated with a ω-(trialkoxysilyl) alkyl bromomethylacetamnide and facially amphiphilic polymer contains a thiol.

Another embodiment of the present invention is a process for attaching a facially amphiphilic polymer to a surface wherein the solid surface is treated with a N-[ω-(trialkoxysilyl)alkyl]maleimide and facially amphiphilic polymer contains a thiol.

Still another embodiment of the present invention is a process for attaching a facially amphiphilic polymer to a surface wherein the surface is gold and the facially amphiphiic polymer contains a thiol.

A variety of polymers are used in a host of medical applications which require sterile surfaces. Catheters, like venous or urinary catheters are cause serious infections. Polyurethane based tubing is by far the major source of commercial catheter tubing. Amphiphilic polymers can be incorporated into polyurethane and other polymers using pre- and post manufacture techniques. The advantage of pre-manufacture incorporation is simpler modification strategies and dispersion of the antimicrobial agent throughout the tubing materials. Tubing manufacturing is typically an extrusion process in which pellets of polyurethane are heated and pressed through a dye producing tubing of the desired diameter. The thermal stability of urethane bonds is very similar to amide and urea bonds again suggesting that thermal processed conditions should not be a problem.

For the pre-manufacture approach, designed antimicrobial polymers are added to the original polyurethane pellets before extrusion resulting in a uniform dispersion throughout the extruded polymer.

Post-manufacture modifications are also possible although in this case the antimicrobial polymer will only be present on the surface of the tubing. However, since catheters have a minimal life cycle it is likely that surface treatment will render the materials sufficiently sanitary for their application. There are a variety of methods one can use to modify polymeric surfaces (E. Piskin *J. Biomat. Sci.-Polymer Ed.* 1992 4:45-60). The most common technique to covalent attach a amphiphilic polymer to the surface relies on irradiation to produce free radicals that form covalent bonds between the polymer and active surface agent. Unfortunately, this process is completely random with no control over orientation or functional group attachment to the surface. Alternatively, photo or chemical oxidation of the polyurethane surface can create carboxylic acid or alcohol fumctionality which will be reactive toward these antimicrobial polymers (the cationic side chains or cationic end groups). The most common technique for surface oxidation is plasma etching (E. Piskin loc. cit.; S. H. Hsu and W. C. Chen, *Biomaterials* 2000 21:359-67) although ozone can also be used. After oxidation, the surface is treated with a bifunctional epoxide followed by addition of the cationic antimicrobial polymer which can react with the epoxide.

Microbial growth in paint and on the surface of paint films also remains an unsolved problem. This can occur in the wet formulated paint or by microbial growth on the dried surface. The paint industry currently uses either isothiazolones or "formaldehyde releasers" for wet paint protection from microbes (G. Sekaran et al. *J. Applied Polymer Sci.* 2001 81:1567-1571; T. J. Kelly et al. *Environ. Sci. Technol.* 1999 33:81-88; M. Sondossi et al. *International Biodeterioration & Biodegradation* 1993 32:243-61). Both of these products are harmful to human beings and great lengths and expense are taken at the factory to limit employee exposure; however, there is no viable alternative currently for the industry. Isothiazolones are used mainly for their effectiveness against *Pseudomonas aeruginosa* and that the antimicrobial polymers discussed in preliminary data are active against this strain.

Any object that is exposed to or susceptible to bacterial or microbial contamination can be treated with these polymers. These needs are particularly acute in the health care and food industries. A growing concern with preservatives has produced a need for new materials that prevent microbiological contamination without including preservatives. The incidence of infection from food-borne pathogens is a continuing concern and antimicrobial packaging material, utensils and surfaces would be valuable. In the health care and medical device areas the utility of antimicrobial instruments, packaging and surfaces are obvious. Products used internally or externally in humans or animal health including, but not limited to, surgical gloves, implanted devices, sutures, catheters, dialysis membranes, water filters and implements, all can harbor and transmit pathogens. The polymers of the present invention can be incorporated into spinnable fibers for use in materials susceptible to bacterial contamination including fabrics, surgical gowns, and carpets. Ophthalmic solutions and contact lenses easily become contaminated and cause ocular infections. Antimicrobial storage containers for contact lens and cleaning solutions would be very valuable. Both pets and agronomic animals are exposed to and harbor a variety of infectious pathogenic organisms that can cause disease in animals or humans.

An embodiment of the current invention is a antimicrobial composition comprising a facially amphiphilic polymer and a composition selected form the group consisting of paint, coatings, lacquer, varnish, caulk, grout, adhesives, resins, films, cosmetic, soap and detergent.

Another embodiment of the present invention is an improved catheter, the improvement comprising incorporating or attaching a facially amphiphilic polymer therein or thereto.

Yet another embodiment of the present invention is an improved contact lens, the improvement comprising incorporating or attaching an amphiphilic polymer therein or thereto.

An embodiment of the present invention is improved plastic devices for the hospital and laboratory the improvement comprising incorporating or attaching a facially amphiphilic polymer therein or thereto.

A further embodiment of the present invention is an improved woven and nonwoven fabrics for hospital use the improvement comprising the incorporating or attaching a facially amphiphilic polymer therein or thereto.

The following examples will serve to further typify the nature of this invention but should not be construed as a limitation in the scope thereof, which scope is defined solely by the appended claims.

The following examples will serve to further typify the nature of this invention but should not be construed as a limitation in the scope thereof, which scope is defined solely by the appended claims.

EXAMPLE 1

Phenylene Ethynylene Synthesis (FIG. 3)

A dried air-free flask was charged with m-diethynyl-benzene (0.037 g, 0.284 mmole, 1.03 eq), the diiodo monomer 3 (0.157 g, 0.275 mmole, 1.00 eq), 3 mol % $Pd(PPh_3)_4$ (0.009 g), CuI (0.003 g, 0.017 mmole, 0.06 eq), 5 mL toluene, and 2 mL diisopropylamine. The solution was flushed under nitrogen, stirring, and then placed in an oil bath at 70° C. for 12 h. The solution was poured into rapidly stirring methanol and the precipitate collected. After drying overnight in vacuuo, the molecular weight of the protected polymer 5 was determined.

7a: $NP=CH_2CH_2CH_2CH_2CH_3$, P=benzyl amine, Mn=17,400, PDI=2.2
7b: $NP=(S)—CH_2CH(CH_3)CH_2CH_3$, P=benzyl amine, Mn=9,780, PDI=1.4

The polymer (50 mg) was taken up in 4M HCl/dioxane at 0° C. and then allowed to warm to room temperature for 12 h. The solvent was removed in vacuuo and the solid titurated with ether three times before drying overnight.

EXAMPLE 2

General Method for Arylene Polymerization-Suzuki Coupling

A dried flask is charged with equal molar ratios of the dibromide and the diboronic acid in toluene. A palladium catalyst, e.g., $Pd(O)Cl_2(PPh_3)_2$ is added, the reaction covered from light, and stirred at 80° C. overnight under positive $N_2$ pressure. The solvent is removed and the solid triturated with $CH_2Cl_2$/hexane. The degree of polymerization is controlled by the addition of various molar amounts of a monofunctional aryl bromide. The molar amount of the aryl bromide is determined by the Flory equation.

EXAMPLE 3

Antimicrobial Assays

The inhibition studies will be carried out in suspension using BHI medium inoculated with bacteria ($10^6$ CFU/ml) in a 96-well format. A stock solution of the polymers was prepared DMSO/water and used to prepare a ten fold dilution series. Minimal inhibitory concentrations (MIC) were obtained by incubating the compounds with the bacteria for 18 hours at 37° C., and measuring cell growth by monitoring at 590 nm.

All references cited in the application are hereby incorporated in their entirety into this specification. Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. Details of the structure may be varied substantially without departing from the spirit of the invention and the exclusive use of all modifications which come within the scope of the appended claim is reserved.

We claim:

1. A polymer or oligomer of formula I

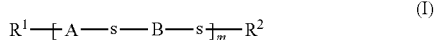

wherein:
A and B are o- or m-phenylene wherein one of A or B is substituted with a polar (P) group and a nonpolar (NP) group and the other of A or B is substituted with neither a polar (P) group nor a nonpolar (NP) group;
s is C≡C—;
$R^1$ is (i) halo and $R^2$ is hydrogen; or (ii)C-s-B-s- and $R^2$ is C; or, (iii)C-s- and $R^2$ is -A-s-C wherein C is pyridine or phenyl said pyridine or phenyl optionally substituted with 1 or 2 substituents independently selected from the group consisting of halo, nitro, cyano, $C_1$-$C_6$alkoxy, $C_1$-$C_6$alkoxycarbonyl, and benzyloxycarbonyl;

NP is a nonpolar group independently selected from $R^4$ or —U—$(CH_2)_p$—$R^4$ wherein $R^4$ is selected from the group consisting of hydrogen, $C_1$-$C_{10}$ alkyl, $C_3$-$C_{18}$ branched alkyl, $C_3$-$C_8$cycloalkyl, monocyclic or polycyclic phenyl optionally substituted with one or more $C_1$-$C_4$ alkyl or halo groups, and monocyclic or polycyclic heteroaryl optionally substituted with one or more $C_1$-$C_4$ alkyl or halo groups, and U and p are as defined below;

P is a polar group selected from the group consisting of III, hydroxyethoxymethyl, methoxyethoxymethyl and polyoxyethylene $$—U—(CH_2)_p—V \qquad (III)$$

wherein:
U is absent or selected from the group consisting of O, S, S(=O), S(=O)$_2$, NH, —C(=O)O—, —C(=O)NH—, —C(=O)S—, —C(=S)NH—, —S(=O)$_2$NH—, and C(=NO—) wherein groups with two chemically nonequivalent termini can adopt both possible orientations;

V is selected from the group consisting of amino, hydroxyl, $C_1$-$C_6$alkylamino, $C_1$-$C_6$dialkylamino, NH$(CH_2)_p$NH$_2$, N$(CH_2CH_2NH_2)_2$, amidine, guanidine, semicarbazone, basic heterocycle, and phenyl optionally substituted with an amino, $C_1$-$C_6$alkylamino, $C_1$-$C_6$dialkylamino and lower acylamino optionally substituted with one or more amino, lower alkylamino or lower dialkylamino;

and the alkylene chain is optionally substituted with an amino or hydroxyl group or unsaturated;
p is independently 0 to 8; and,
m is 2 to about 500.

2. The polymer or oligomer of claim 1 wherein:
NP is a nonpolar group independently selected from $R^4$ or —U—$(CH_2)_p$—$R^4$ wherein $R^4$ is selected from the group consisting of hydrogen, $C_1$-$C_4$ alkyl, $C_3$-$C_{12}$ branched alkyl, $C_3$-$C_8$cycloalkyl, phenyl optionally substituted with one or more $C_1$-$C_4$ alkyl groups and heteroaryl optionally substituted with one or more $C_1$-$C_4$ alkyl groups and U and p are as defined below;

P is a polar group selected from the group consisting of III, hydroxyethoxymethyl, methoxyethoxymethyl and polyoxyethylene $$—U—(CH_2)_p—V \qquad (III)$$

wherein:
U is absent, O, S, SO, SO$_2$, or NH;
V is selected from the group consisting of amino, hydroxyl, $C_1$-$C_6$alkylamino, $C_1$-$C_6$dialkylamino, NH$(CH_2)_p$NH$_2$, N$(CH_2CH_2NH_2)_2$, amidine, guanidine, semicarbazone, imidazole, piperidine, piperazine, 4-alkylpiperazine and phenyl optionally substituted with an amino, $C_1$-$C_6$alkylamino, $C_1$-$C_6$dialkylamino and lower acylamino optionally substituted with one or more amino, lower alkylamino or lower dialkylamino;
the alkylene chain is optionally substituted with an amino or hydroxyl group or unsaturated; and
m is 2 to about 500.

3. The polymer or oligomer of claim 1 wherein:
A and B are each m-phenylene;
NP is a nonpolar group independently selected from $R^4$ or —U—$(CH_2)_p$—$R^4$ wherein $R^4$ is selected from the group consisting of hydrogen, methyl, ethyl, n-propyl, iso-propyl, n-butyl, iso-butyl, sec-butyl, tert-butyl, n-pentyl, iso-pentyl, and sec-pentyl and U and p are as defined below;

P is a polar group U—$(CH_2)_p$—V wherein U is absent or selected from the group consisting of O and S, and V is selected from the group consisting of amino, lower alkyl amino, lower dialkylamino, imidazole, guanidine, NH$(CH_2)_p$NH$_2$, N$(CH_2CH_2NH_2)_2$, piperidine, piperazine, and 4-alkylpiperazine;
p is independently 0 to 8; and
m is 2 to about 500.

4. A polymer or oligomer of formula XIX

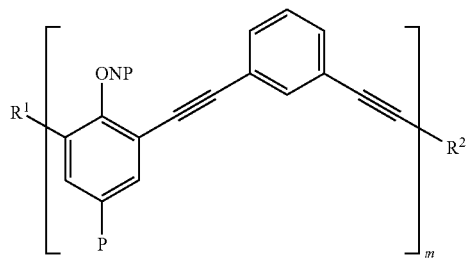

(XIX)

wherein
NP is methyl, ethyl, n-propyl, iso-propyl, n-butyl, iso-butyl, n-butyl, sec-butyl, tert-butyl, n-pentyl, iso-pentyl, or sec-pentyl;
P is a polar group U—$(CH_2)_p$—V wherein U is O or S, p is 0 to 8 and V is selected from the group consisting of amino, lower alkyl amino, lower dialkylamino, guanidine, pyridine, piperazine, and 4-alkylpiperazine;
p is 0 to 8; and,
m is 2 to about 30.

5. A method of killing microorganisms, said method comprising:
providing a substrate having disposed thereon a contact killing, facially amphiphilic polymer or oligomer of claim 1; and
placing said facially amphiphilic polymer or oligomer disposed thereon on said substrate in contact with a microorganism.

6. The method of claim 5 wherein said substrate is selected from the group consisting of wood, synthetic polymers, plastics, natural and synthetic fibers, cloth, paper, rubber and glass.

7. The method of claim 6 wherein said substrate is from a plastic selected from the group consisting of polysulfone, polyacrylate, polyurea, polyethersulfone, polyamide, polycarbonate, polyvinylidenefluoride, polyethylene, polypropylene and cellulosics.

8. A microbiocidal composition comprising a solid support selected from the group consisting of wood, synthetic polymers, natural and synthetic fibers, cloth, paper, rubber and glass, wherein said solid support incorporates, attaches or is coated with a facially amphiphilic polymer or oligomer of claim 1.

9. The microbiocidal composition of claim 8 wherein said solid support is a plastic selected from the group consisting of polysulfone, polyacrylate, polyethersulfone, polyamide, polycarbonate, polyvinylidenefluoride, polyethylene, polypropylene and cellulosics.

10. A process for producing an antimicrobial surface by attaching an antimicrobial facially amphiphilic polymer or oligomer of claim 1 to a surface comprising treating said surface with a first chemically reactive group and reacting a facially amphiphilic polymer or oligomer linked to a second reactive group thereto.

11. The process of claim 10 wherein said first reactive group is a 1-(trialkoxysilyl)propylamine and said second reactive group is an activated carboxylic acid.

12. The process of claim 10 wherein said first reactive group is a ω-(trialkoxysilyl)alkyl bromomethylacetamide and said second reactive group is a thiol.

13. The process of claim 10 wherein said first reactive group is a N-[ω-(trialkoxysilyl)alkyl]maleimide and said second reactive group is a thiol.

14. The process of claim 10 wherein the first reactive group is a gold surface and said second reactive group is a thiol.

15. An antimicrobial composition comprising a composition selected from the group consisting of paint, coatings, lacquer, varnish, caulk, grout, adhesives, resins, films, cosmetic, soap and detergent, wherein said composition incorporates or disperses throughout a facially amphiphilic polymer or oligomer of claim 1.

16. An improved catheter, the improvement comprising incorporating or attaching an antimicrobial facially amphiphilic polymer or oligomer of claim 1 therein or thereto said catheter.

17. An improved contact lens, the improvement comprising incorporating or attaching an antimicrobial facially amphiphilic polymer or oligomer of claim 1 therein or thereto said contact lens.

18. An improved plastic device for the hospital and laboratory, the improvement comprising incorporating or attaching an antimicrobial facially amphiphilic polymer or oligomer of claim 1 therein or thereto said plastic device.

19. An improved woven or nonwoven fabric for hospital use, the improvement comprising incorporating or attaching an antimicrobial facially amphiphilic polymer or oligomer of claim 1 therein or thereto said fabric.

20. A microbiocidal composition comprising a medical device or medical product, wherein said medical device incorporates, attaches or is coated with a facially amphiphilic polymer or oligomer of claim 1 therein or thereto.

21. The medical device or medical product of claim 20, wherein said medical device or medical product is selected from the group consisting of surgical gloves, implanted devices, sutures, catheters, dialysis membranes, and water filters and implements.

22. A microbiocidal composition comprising a material comprising spinnable fibers, wherein said fibers incorporate or attach a facially amphiphilic polymer or oligomer of claim 1 therein or thereto.

23. The material comprising spinnable fibers of claim 22, wherein said material is selected from the group consisting of fabrics, surgical gowns, and carpets.

24. The polymer or oligomer of claim 1, wherein one of A or B is substituted at the 2-position with the polar (P) group and the 5-position with the nonpolar (NP) group and the other of A or B is substituted by neither a polar (P) group nor a nonpolar (NP) group.

25. The polymer or oligomer of claim 24, wherein P is a polar group U—$(CH_2)_p$—V wherein U is absent or selected from the group consisting of O and S, and V is selected from the group consisting of amino, lower alkyl amino, lower dialkylamino, imidazole, guanidine, $NH(CH_2)_pNH_2$, $N(CH_2CH_2NH_2)_2$, piperidine, piperazine, and 4-alkylpiperazine.

26. The polymer or oligomer of claim 25, wherein U is absent.

27. The polymer or oligomer of claim 1, wherein m is 2 to about 30.

\* \* \* \* \*